United States Patent
Wang et al.

(10) Patent No.: US 10,435,466 B2
(45) Date of Patent: Oct. 8, 2019

(54) ANTI-TIM-3 ANTIBODIES

(71) Applicant: Agency for Science, Technology and Research, Connexis (SG)

(72) Inventors: Cheng-i Wang, Singapore (SG); Hsueh Ling Janice Oh, Singapore (SG); Siok Ping Yeo, Singapore (SG); Yun Pei Sharon Goh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 50 days.

(21) Appl. No.: 15/521,514

(22) PCT Filed: Oct. 27, 2015

(86) PCT No.: PCT/SG2015/050414
§ 371 (c)(1),
(2) Date: Apr. 24, 2017

(87) PCT Pub. No.: WO2016/068802
PCT Pub. Date: May 6, 2016

(65) Prior Publication Data
US 2017/0306016 A1    Oct. 26, 2017

(30) Foreign Application Priority Data

Oct. 27, 2014 (GB) .................................. 1419094.6

(51) Int. Cl.
*C07K 16/28* (2006.01)
*A61K 39/395* (2006.01)

(52) U.S. Cl.
CPC ........ *C07K 16/2803* (2013.01); *A61K 39/395* (2013.01); *C07K 16/2809* (2013.01); *C07K 16/28* (2013.01); *C07K 2317/31* (2013.01); *C07K 2317/622* (2013.01)

(58) Field of Classification Search
CPC .............. C07K 16/28; C07K 2317/622; C07K 2317/31
USPC .......................................... 424/133.1, 178.1
See application file for complete search history.

(56) References Cited

U.S. PATENT DOCUMENTS

| | | | |
|---|---|---|---|
| 8,067,544 | B2 | 11/2011 | Landes et al. |
| 8,552,156 | B2 | 10/2013 | Takayanagi et al. |
| 2003/0103978 | A1 | 6/2003 | Deshpande et al. |
| 2011/0318339 | A1 | 12/2011 | Smider et al. |
| 2012/0189617 | A1 | 7/2012 | Takayanagi et al. |
| 2013/0022623 | A1 | 1/2013 | Karsunky et al. |
| 2017/0240633 | A1 | 8/2017 | Wang et al. |

FOREIGN PATENT DOCUMENTS

| | | |
|---|---|---|
| CN | 102392038 A | 3/2012 |
| CN | 102492038 A | 6/2012 |
| CN | 103936853 A | 7/2014 |
| CN | 104592388 A | 5/2015 |
| EP | 0873363 B1 | 10/2010 |
| EP | 2417984 A1 | 2/2012 |
| ES | 2192426 A1 | 10/2003 |
| WO | WO-2004-050683 A2 | 6/2004 |
| WO | WO-2006-138729 A2 | 12/2006 |
| WO | WO-2007-059082 A1 | 5/2007 |
| WO | WO-2010-014854 A2 | 2/2010 |
| WO | WO-2011-130417 A2 | 10/2011 |
| WO | WO-2011-159877 A2 | 12/2011 |
| WO | WO-2012-092539 A2 | 7/2012 |
| WO | WO-2013-006490 A2 | 1/2013 |
| WO | WO-2014-022332 A1 | 2/2014 |
| WO | WO-2014-070874 A1 | 5/2014 |
| WO | WO-2014-116846 A2 | 7/2014 |
| WO | WO-2015-103072 A1 | 7/2015 |
| WO | WO-2015-117002 A1 | 8/2015 |
| WO | WO-2016-068802 A1 | 5/2016 |
| WO | WO-2016-068803 A1 | 5/2016 |

OTHER PUBLICATIONS

Barber et al. (2006) Nature 439:682-687 "Restoring function in exhausted CD8 T cells during chronic viral infection".
Butler et al. (2012) Nature Immunology 13(2):188-195 "Therapeutic blockade of PDL-L1 and LAG-3 rapidly clears established blood-stage Plasmodium infection".
International Preliminary Report on Patentability dated Nov. 14, 2016 in PCT/SG2015/050415.
International Preliminary Report on Patentability dated May 2, 2017 in PCT/SG2015/050414.
International Search Report dated Dec. 21, 2015 in PCT/SG2015/050414.
International Search Report dated Dec. 21, 2015 in PCT/SG2015/050415.
Lum and Thakur (2011) BioDrugs 25(6):365-379 "Targeting T Cells with Bispecific Antibodies for Cancer Therapy".
McMahan et al. (2010) The Journal of Clinical Investigation 120(12):4546-4557 "Tim-3 expression of PD-1+ HCV-specific human CTLs is associated with viral persistence, and its blockade restores hepatocyte-directed in vitro cytotoxicity".
Said et al. (2010) Nature Medicine16(4):452-460 "Programmed death-1-induced interleukin-10 production by monocytes impairs CD4+ T cell activation during HIV infection".
Wherry (2011) Nature Immunology 12(6):492-499 "T cell exhaustion".

*Primary Examiner* — Lynn A Bristol
(74) *Attorney, Agent, or Firm* — Adsero IP

(57) ABSTRACT

Anti-TIM-3 antibodies are disclosed, as well as pharmaceutical compositions comprising such antibodies, and uses and methods using the same, such as in the treatment of cancer or infectious disease or T-cell dysfunctional disorders. Bispecific antibodies against TIM-3 and other targets are also disclosed, with a preferred embodiment of a bispecific antibody against TIM-3 and CD3.

9 Claims, 20 Drawing Sheets
Specification includes a Sequence Listing.

1B9 clone

QSVLTQPPSVSAAPGQKVTISC<u>SGSSSNIGNNYVS</u>WYQQLPGTAPKLLIY<u>GNN WRPS</u>GIPDRFSGSKSGTSATLGITGLQTGDEADYYC<u>EAWDYYVAAGY</u>FGGGT KLTVL       (SEQ ID NO:1)

LC-CDR1:      SGSSSNIGNNYVS (SEQ ID NO:10)

LC-CDR2:      GNNWRPS     (SEQ ID NO:11)

LC-CDR3:      EAWDYYVAAGY (SEQ ID NO:12)

1H9 clone

QSVLTQPPSVSAAPGQKVTISC<u>SGSSSNIGNNYVS</u>WYQQLPGTAPKLLIY<u>GNN WRPS</u>GIPDRFSGSKSGTSATLGITGLQTGDEADYYC<u>DSWDSADASGV</u>FGGGT KLTVL       (SEQ ID NO:2)

LC-CDR1:      SGSSSNIGNNYVS (SEQ ID NO:10)

LC-CDR2:      GNNWRPS     (SEQ ID NO:11)

LC-CDR3:      DSWDSADASGV (SEQ ID NO:13)

1H10

QSVLTQPPSVSAAPGQKVTISC<u>SGSSSNIGNNYVS</u>WYQQLPGTAPKLLIY<u>GNN WRPS</u>GIPDRFSGSKSGTSATLGITGLQTGDEADYYC<u>DSWDYDYAAGV</u>FGGGT KLTVL       (SEQ ID NO:3)

LC-CDR1:      SGSSSNIGNNYVS (SEQ ID NO:10)

LC-CDR2:      GNNWRPS     (SEQ ID NO:11)

LC-CDR3:      DSWDYDYAAGV (SEQ ID NO:14)

Figure 1

2C7 clone

QSVLTQPPSVSAAPGQKVTISC<u>SGSSSNIGNNYVS</u>WYQQLPGTAPKLLIY<u>GNN
WRPS</u>GIPDRFSGSKSGTSATLGITGLQTGDEADYYC<u>DSWDSYLAAGV</u>FGGGT
KLTVL          (SEQ ID NO:4)

LC-CDR1:       SGSSSNIGNNYVS (SEQ ID NO:10)

LC-CDR2:       GNNWRPS      (SEQ ID NO:11)

LC-CDR3:       DSWDSYLAAGV (SEQ ID NO:15)

2F4 clone

QSVLTQPPSVSAAPGQKVTISC<u>SGSSSNIGNNYVS</u>WYQQLPGTAPKLLIY<u>GNN
WRPS</u>GIPDRFSGSKSGTSATLGITGLQTGDEADYYC<u>ESWDYDYASGV</u>FGGGT
KLTVL          (SEQ ID NO:5)

LC-CDR1:       SGSSSNIGNNYVS (SEQ ID NO:10)

LC-CDR2:       GNNWRPS      (SEQ ID NO:11)

LC-CDR3:       ESWDYDYASGV (SEQ ID NO:16)

2G6 clone

QSVLTQPPSVSAAPGQKVTISC<u>SGSSSNIGNNYVS</u>WYQQLPGTAPKLLIY<u>GNN
WRPS</u>GIPDRFSGSKSGTSATLGITGLQTGDEADYYC<u>DSWDSSDSSGV</u>FGGGT
KLTVL          (SEQ ID NO:6)

LC-CDR1:       SGSSSNIGNNYVS (SEQ ID NO:10)

LC-CDR2:       GNNWRPS      (SEQ ID NO:11)

LC-CDR3:       DSWDSSDSSGV (SEQ ID NO:17)

Figure 1 (Cont.)

1D9 clone

QSVLTQPPSVSAAPGQKVTISC<u>SGSSSNIGNNYV</u>SWYQQLPGTAPKLLIY<u>GNN
WRPS</u>GIPDRFSGSKSGTSATLGITGLQTGDEADYYC<u>EAWDSAYAAGS</u>FGGGT
KLTVL          (SEQ ID NO:7)

LC-CDR1:     SGSSSNIGNNYV  (SEQ ID NO:10)

LC-CDR2:     GNNWRPS     (SEQ ID NO:11)

LC-CDR3:     EAWDSAYAAGS  (SEQ ID NO:18)

1F4 clone

QSVLTQPPSVSAAPGQKVTISC<u>SGSSSNIGNNYV</u>SWYQQLPGTAPKLLIY<u>GNN
WRPS</u>GIPDRFSGSKSGTSATLGITGLQTGDEADYYC<u>DSWDAALSAGV</u>FGGGT
KLTVL          (SEQ ID NO:8)

LC-CDR1:     SGSSSNIGNNYVS (SEQ ID NO:10)

LC-CDR2:     GNNWRPS     (SEQ ID NO:11)

LC-CDR3:     DSWDAALSAGV  (SEQ ID NO:19)

2C8 clone

QSVLTQPPSVSAAPGQKVTISC<u>SGSSSNIGNNYV</u>SWYQQLPGTAPKLLIY<u>GNN
WRPS</u>GIPDRFSGSKSGTSATLGITGLQTGDEADYYC<u>ESWDAAAAGY</u>FGGGT
KLTVL          (SEQ ID NO:9)

LC-CDR1:     SGSSSNIGNNYVS (SEQ ID NO:10)

LC-CDR2:     GNNWRPS     (SEQ ID NO:11)

LC-CDR3:     ESWDAAAAGY  (SEQ ID NO:20)

Figure 1 (Cont.)

1B9 clone

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGSDA</u>
WGQGTLVTVSS    (SEQ ID NO:21)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGSDA | (SEQ ID NO:32) |

1H9 clone

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGFDD</u>
WGQGTLVTVSS    (SEQ ID NO:22)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGFDD | (SEQ ID NO:33) |

1H10

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGFDS</u>
WGQGTLVTVSS    (SEQ ID NO:23)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGFDS | (SEQ ID NO:34) |

Figure 2

2C7 clone

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGYDY</u>
WGQGTLVTVSS    (SEQ ID NO:24)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGYDY | (SEQ ID NO:35) |

2F4 clone

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGSDA</u>
WGQGTLVTVSS    (SEQ ID NO:25)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGSDA | (SEQ ID NO:36) |

2G6 clone

QVQLQQWGAGLLKPSETLSLTCAVY<u>GGSFSGYYWS</u>WIRQPPGKGLEWIG<u>EIN
HSGSTNYNPSLKS</u>RVTISVDTSKNQFSLKLSSVTAADTAVYYCAR<u>GYVAGFDS</u>
WGQGTLVTVSS    (SEQ ID NO:26)

| | | |
|---|---|---|
| HC-CDR1: | GGSFSGYYWS | (SEQ ID NO:30), or |
| | GYYWS | (SEQ ID NO:61) |
| HC-CDR2: | EINHSGSTNYNPSLKS | (SEQ ID NO:31) |
| HC-CDR3: | GYVAGFDS | (SEQ ID NO:37) |

Figure 2 (Cont.)

1D9 clone

QVQLQQWGAGLLKPSETLSLTCAVY<u>GGSFSGYYWS</u>WIRQPPGKGLEWIG<u>EIN</u>
<u>HSGSTNYNPSLKS</u>RVTISVDTSKNQFSLKLSSVTAADTAVYYCAR<u>GYYAGDDY</u>
WGQGTLVTVSS   (SEQ ID NO:27)

HC-CDR1:    GGSFSGYYWS    (SEQ ID NO:30), or

GYYWS    (SEQ ID NO:61)

HC-CDR2:    EINHSGSTNYNPSLKS    (SEQ ID NO:31)

HC-CDR3:    GYYAGDDY    (SEQ ID NO:38)

1F4 clone

QVQLQQWGAGLLKPSETLSLTCAVY<u>GGSFSGYYWS</u>WIRQPPGKGLEWIG<u>EIN</u>
<u>HSGSTNYNPSLKS</u>RVTISVDTSKNQFSLKLSSVTAADTAVYYCAR<u>GYVAGYDY</u>
WGQGTLVTVSS   (SEQ ID NO:28)

HC-CDR1:    GGSFSGYYWS    (SEQ ID NO:30), or

GYYWS    (SEQ ID NO:61)

HC-CDR2:    EINHSGSTNYNPSLKS    (SEQ ID NO:31)

HC-CDR3:    GYVAGYDY    (SEQ ID NO:39)

2C8 clone

QVQLQQWGAGLLKPSETLSLTCAVY<u>GGSFSGYYWS</u>WIRQPPGKGLEWIG<u>EIN</u>
<u>HSGSTNYNPSLKS</u>RVTISVDTSKNQFSLKLSSVTAADTAVYYCAR<u>GYVAGSDA</u>
WGQGTLVTVSS   (SEQ ID NO:29)

HC-CDR1:    GGSFSGYYWS    (SEQ ID NO:30), or

GYYWS    (SEQ ID NO:61)

HC-CDR2:    EINHSGSTNYNPSLKS    (SEQ ID NO:31)

HC-CDR3:    GYVAGSDA    (SEQ ID NO:40)

Figure 2 (Cont.)

| Clone | CDR L1 | CDR L2 | CDR L3 |
|---|---|---|---|
| Light Chain | | | |
| 1B9 | SGSSSNIGNNYVS (SEQ ID NO:10) | GNNWRPS (SEQ ID NO:11) | EAWDYYVAAGY (SEQ ID NO:12) |
| 1H9 | SGSSSNIGNNYVS (SEQ ID NO:10) | GNNWRPS (SEQ ID NO:11) | DSWDSADASGV (SEQ ID NO:13) |
| 1H10 | SGSSSNIGNNYVS (SEQ ID NO:10) | GNNWRPS (SEQ ID NO:11) | DSWDYDYAAGV (SEQ ID NO:14) |
| 2C7 | SGSSSNIGNNYVS (SEQ ID NO:10) | GNNWRPS (SEQ ID NO:11) | DSWDSYLAAGV (SEQ ID NO:15) |
| 2F4 | SGSSSNIGNNYVS (SEQ ID NO:10) | GNNWRPS (SEQ ID NO:11) | ESWDYDYASGV (SEQ ID NO:16) |
| 2G6 | SGSSSNIGNNYVS (SEQ ID NO:10) | GNNWRPS (SEQ ID NO:11) | DSWDSSDSSGV (SEQ ID NO:17) |
| 1D9 | SGSSSNIGNNYV (SEQ ID NO:10) | GNNWRPS (SEQ ID NO:11) | EAWDSAYAAGS (SEQ ID NO:18) |
| 1F4 | SGSSSNIGNNYVS (SEQ ID NO:10) | GNNWRPS (SEQ ID NO:11) | DSWDAALSAGV (SEQ ID NO:19) |
| 2C8 | SGSSSNIGNNYVS (SEQ ID NO:10) | GNNWRPS (SEQ ID NO:11) | ESWDAAAAAGY (SEQ ID NO:20) |
| Consensus | SGSSSNIGNNYVS (SEQ ID NO:10) | GNNWRPS (SEQ ID NO:11) | $X_1X_2WDX_3X_4X_5X_6X_7GX_8$<br><br>$X_1$= E or D<br>$X_2$= A or S<br>$X_3$= Y, S or A<br>$X_4$= Y, A, D or S<br>$X_5$= V, D, Y, L or A<br>$X_6$= A or S<br>$X_7$= A or S<br>$X_8$= Y, V or S<br><br>(SEQ ID NO:41) |

Figure 3

| Clone | CDR H1 | CDR H2 | CDR H3 |
|---|---|---|---|
| Heavy Chain | | | |
| 1B9 | GGSFSGYYWS (SEQ ID NO:30), or GYYWS (SEQ ID NO:61) | EINHSGSTNYNPSLKS (SEQ ID NO:31) | GYVAGSDA (SEQ ID NO:32) |
| 1H9 | GGSFSGYYWS (SEQ ID NO:30), or GYYWS (SEQ ID NO:61) | EINHSGSTNYNPSLKS (SEQ ID NO:31) | GYVAGFDD (SEQ ID NO:33) |
| 1H10 | GGSFSGYYWS (SEQ ID NO:30), or GYYWS (SEQ ID NO:61) | EINHSGSTNYNPSLKS (SEQ ID NO:31) | GYVAGFDS (SEQ ID NO:34) |
| 2C7 | GGSFSGYYWS (SEQ ID NO:30), or GYYWS (SEQ ID NO:61) | EINHSGSTNYNPSLKS (SEQ ID NO:31) | GYVAGYDY (SEQ ID NO:35) |
| 2F4 | GGSFSGYYWS (SEQ ID NO:30), or GYYWS (SEQ ID NO:61) | EINHSGSTNYNPSLKS (SEQ ID NO:31) | GYVAGSDA (SEQ ID NO:36) |
| 2G6 | GGSFSGYYWS (SEQ ID NO:30), or GYYWS (SEQ ID NO:61) | EINHSGSTNYNPSLKS (SEQ ID NO:31) | GYVAGFDS (SEQ ID NO:37) |
| 1D9 | GGSFSGYYWS (SEQ ID NO:30), or GYYWS (SEQ ID NO:61) | EINHSGSTNYNPSLKS (SEQ ID NO:31) | GYYAGDDY (SEQ ID NO:38) |
| 1F4 | GGSFSGYYWS (SEQ ID NO:30), or GYYWS (SEQ ID NO:61) | EINHSGSTNYNPSLKS (SEQ ID NO:31) | GYVAGYDY (SEQ ID NO:39) |
| 2C8 | GGSFSGYYWS (SEQ ID NO:30), or GYYWS (SEQ ID NO:61) | EINHSGSTNYNPSLKS (SEQ ID NO:31) | GYVAGSDA (SEQ ID NO:40) |
| Consensus | GGSFSGYYWS (SEQ ID NO:30), or GYYWS (SEQ ID NO:61) | EINHSGSTNYNPSLKS (SEQ ID NO:31) | GYZ$_1$AGZ$_2$DZ$_3$<br><br>Z$_1$= V or Y<br>Z$_2$= S, F, Y, D<br>Z$_3$= A, D, S, Y<br>(SEQ ID NO:42) |

Figure 3 (Cont.)

Light chain variable domains

1B9 clone

>1B9_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCEAWDYYVAAGYFGGGTKLTVL [SEQ ID
NO. 1]

>1B9_ntd_L

CAGTCTGTGTTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGAAGCTTGGGATTATTATGTTGCTGCTG
GGTATTTCGGCGGAGGGACCAAGCTGACCGTCCTA [SEQ ID NO. 43]

1H9 clone

>1H9_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCDSWDSADASGVFGGGTKLTVL [SEQ ID
NO. 2]

>1H9_ntd_L

CAGTCTGTGCTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGATTCTTGGGATTCTGCTGATGCTTCTG
GGGTTTTCGGCGGAGGGACCAAGCTGACCGTCCTA [SEQ ID NO. 44]

Figure 4

1H10 clone

>1H10_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCDSWDYDYAAGVFGGGTKLTVL [SEQ ID
NO. 3]

>1H10_ntd_L

CAGTCTGTGCTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGATTCTTGGGATTATGATTATGCTGCTG
GGGTTTTCGGCGGAGGGACCAAGCTGACCGTCCTA [SEQ ID NO. 45]

2C7 clone

>2C7_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCDSWDSYLAAGVFGGGTKLTVL [SEQ ID
NO. 4]

>2C7_ntd_L

CAGTCTGTGTTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGATTCTTGGGATTCTTATCTTGCTGCTG
GGGTTTTCGGCGGAGGGACCAAGCTGACCGTCCTA [SEQ ID NO. 46]

Figure 4 (Cont.)

2F4 clone

>2F4_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCESWDYDYASGVFGGGTKLTVL [SEQ ID
NO. 5]

>2F4_ntd_L

CAGTCTGTGCTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGAATCTTGGGATTATGATTATGCTTCTG
GGGTTTTCGGCGGAGGGACCAAGCTGACCGTCCTA [SEQ ID NO. 47]

2G6 clone

>2G6_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCDSWDSSDSSGVFGGGTKLTVL [SEQ ID
NO. 6]

>2G6_ntd_L

CAGTCTGTGTTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGATTCTTGGGATTCTTCTGATTCTTCTG
GGGTTTTCGGCGGAGGGACCAAGCTGACCGTCCTA [SEQ ID NO. 48]

Figure 4 (Cont.)

1D9 clone

>1D9_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCEAWDSAYAAGSFGGGTKLTVL [SEQ ID
NO. 7]

>1D9_ntd_L

CAGTCTGTGCTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGAAGCTTGGGATTCTGCTTATGCTGCTG
GGTCTTTCGGCGGAGGGACCAAGCTGACCGTCCTA [SEQ ID NO. 49]

1F4 clone

>1F4_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCDSWDAALSAGVFGGGTKLTVL [SEQ ID
NO. 8]

>1F4_ntd_L

CAGTCTGTGTTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGATTCTTGGGATGCTGCTCTTTCTGCTG
GGGTTTTCGGCGGAGGGACCAAGCTGACCGTCCTA [SEQ ID NO. 50]

Figure 4 (Cont.)

2C8 clone

>2C8_aa_L

QSVLTQPPSVSAAPGQKVTISCSGSSSNIGNNYVSWYQQLPGTAPKLLIYGNNWRPSGI
PDRFSGSKSGTSATLGITGLQTGDEADYYCESWDAAAAAGYFGGGTKLTVL [SEQ ID
NO. 9]

>2C8_ntd_L

CAGTCTGTGCTGACGCAGCCGCCCTCAGTGTCTGCGGCCCCAGGACAGAAAGTCACCAT
CTCCTGCTCTGGAAGCAGCTCCAACATTGGGAATAATTATGTATCCTGGTACCAGCAGC
TCCCAGGAACAGCCCCCAAACTCCTCATTTATGGCAATAATTGGCGACCCTCAGGGATT
CCTGACCGCTTCTCTGGCTCCAAGTCTGGCACCTCAGCCACCCTGGGCATCACCGGACT
TCAGACTGGGGACGAGGCCGATTATTACTGCGAATCTTGGGATGCTGCTGCTGCTGCTG
GGTATTTCGGCGGAGGGACCAAGCTGACCGTCCTA [SEQ ID NO. 51]

Heavy chain variable domains

1B9 clone

>1B9_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGSDAWGQGTLVTVSS
[SEQ ID NO. 21]

>1B9_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTCTGATGCTTGGGGCCAGGGAACCCTGGTCACCGTCTCAAGC   [SEQ
ID NO. 52]

Figure 4 (Cont.)

1H9 clone

>1H9_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGFDDWGQGTLVTVSS
[SEQ ID NO. 22]

>1H9_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTTTGATGATTGGGGCCAGGGAACCCTGGTCACCGTCTCAAGC  [SEQ
ID NO. 53]

1H10 clone

>1H10_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGFDSWGQGTLVTVSS
[SEQ ID NO. 23]

>1H10_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTTTGATTCTTGGGGCCAGGGAACCCTGGTCACCGTCTCAAGC  [SEQ
ID NO. 54]

Figure 4 (Cont.)

2C7 clone

>2C7_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGYDYWGQGTLVTVSS
[SEQ ID NO. 24]

>2C7_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTATGATTATTGGGGCCAGGGAACCCTGGTCACCGTCTCAAGC    [SEQ
ID NO. 55]

2F4 clone

>2F4_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGSDAWGQGTLVTVSS
[SEQ ID NO. 25]

>2F4_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTCTGATGCTTGGGGCCAGGGAACCCTGGTCACCGTCTCAAGC    [SEQ
ID NO. 56]

Figure 4 (Cont.)

2G6 clone

>2G6_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGFDSWGQGTLVTVSS
[SEQ ID NO. 26]

>2G6_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTTTGATTCTTGGGGCCAGGGAACCCTGGTCACCGTCTCAAGC   [SEQ
ID NO. 57]

1D9 clone

>1D9_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYYAGDDYWGQGTLVTVSS
[SEQ ID NO. 27]

>1D9_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATTATGCTGGCGATGATTATTGGGGCCAGGGAACCCTGGTCACCGTCTCAAGC   [SEQ
ID NO. 58]

Figure 4 (Cont.)

1F4 clone

>1F4_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGYDYWGQGTLVTVSS
[SEQ ID NO. 28]

>1F4_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTATGATTATTGGGGCCAGGGAACCCTGGTCACCGTCTCAAGC     [SEQ
ID NO. 59]

2C8 clone

>2C8_aa_H

QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARGYVAGSDAWGQGTLVTVSS
[SEQ ID NO. 29]

>2C8_ntd_H

CAGGTGCAGCTACAGCAGTGGGGCGCAGGACTGTTGAAGCCTTCGGAGACCCTGTCCCT
CACCTGCGCTGTCTATGGTGGGTCCTTCAGTGGTTACTACTGGAGCTGGATCCGCCAGC
CCCCAGGGAAGGGGCTGGAGTGGATTGGGGAAATCAATCATAGTGGAAGCACCAACTAC
AACCCGTCCCTCAAGAGTCGAGTCACCATATCAGTAGACACGTCCAAGAACCAGTTCTC
CTTGAAACTGAGCTCTGTGACCGCCGCGGACACGGCTGTGTATTACTGTGCGAGAGGCT
ATGTTGCTGGCTCTGATGCTTGGGGCCAGGGAACCCTGGTCACCGTCTCAAGC     [SEQ
ID NO. 60]

Figure 4 (Cont.)

| Clones | Off rate in SPR assay with culture supernatants Kd (s$^{-1}$) | Off rate in SPR assay with crude periplasmic extracts Kd (s$^{-1}$) |
|---|---|---|
| 1H10 | 2.9x10$^{-5}$ | 2.3x10$^{-5}$ |
| 1B9 | 4.3x10$^{-5}$ | 2.8x10$^{-5}$ |
| 2F4 | 8.7x10$^{-5}$ | 1.4x10$^{-4}$ |
| 2G6 | 1.3x10$^{-4}$ | 2.2x10$^{-4}$ |
| 1H9 | 1.6x10$^{-4}$ | 7.0x10$^{-5}$ |
| 1D9 | 1.8x10$^{-4}$ | 1.8x10$^{-4}$ |
| 2C7 | 2.1x10$^{-4}$ | 1.9x10$^{-4}$ |
| 1F4 | 3.0x10$^{-4}$ | 2.9x10$^{-4}$ |
| 2C8 | 4.1x10$^{-4}$ | 3.9x10$^{-4}$ |

Figure 5

SEQUENCE LISTING

```
<160> NUMBER OF SEQ ID NOS: 61

<210> SEQ ID NO 1
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 1B9

<400> SEQUENCE: 1

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Asn Trp Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Ala Trp Asp Tyr Tyr Val
                85                  90                  95

Ala Ala Gly Tyr Phe Gly Gly Gly Thr Lys Leu Thr Val Leu
            100                 105                 110
```

```
<210> SEQ ID NO 2
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 1H9

<400> SEQUENCE: 2

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Asn Trp Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Asp Ser Trp Asp Ser Ala Asp
                85                  90                  95

Ala Ser Gly Val Phe Gly Gly Gly Thr Lys Leu Thr Val Leu
                100                 105                 110

<210> SEQ ID NO 3
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 1H10

<400> SEQUENCE: 3

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Asn Trp Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Asp Ser Trp Asp Tyr Asp Tyr
                85                  90                  95

Ala Ala Gly Val Phe Gly Gly Gly Thr Lys Leu Thr Val Leu
                100                 105                 110

<210> SEQ ID NO 4
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 2C7

<400> SEQUENCE: 4

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
```

```
                    20                  25                  30

Tyr Val Ser Trp Tyr Gln Gln Leu Pro Gly Thr Ala Pro Lys Leu Leu
            35                  40                  45

Ile Tyr Gly Asn Asn Trp Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                 70                  75                  80

Thr Gly Asp Glu Ala Asp Tyr Tyr Cys Asp Ser Trp Asp Ser Tyr Leu
                85                  90                  95

Ala Ala Gly Val Phe Gly Gly Gly Thr Lys Leu Thr Val Leu
            100                 105                 110

<210> SEQ ID NO 5
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 2F4

<400> SEQUENCE: 5

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly Asn Asn Trp Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                 70                  75                  80

Thr Gly Asp Glu Ala Asp Tyr Tyr Cys Glu Ser Trp Asp Tyr Asp Tyr
                85                  90                  95

Ala Ser Gly Val Phe Gly Gly Gly Thr Lys Leu Thr Val Leu
            100                 105                 110

<210> SEQ ID NO 6
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 2G6

<400> SEQUENCE: 6

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly Asn Asn Trp Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                 70                  75                  80

Thr Gly Asp Glu Ala Asp Tyr Tyr Cys Asp Ser Trp Asp Ser Ser Asp
                85                  90                  95

Ser Ser Gly Val Phe Gly Gly Gly Thr Lys Leu Thr Val Leu
```

-continued

<210> SEQ ID NO 7
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 1D9

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Asn Trp Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Ala Trp Asp Ser Ala Tyr
                85                  90                  95

Ala Ala Gly Ser Phe Gly Gly Gly Thr Lys Leu Thr Val Leu
            100                 105                 110

<210> SEQ ID NO 8
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 1F4

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Asn Trp Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Asp Ser Trp Asp Ala Ala Leu
                85                  90                  95

Ser Ala Gly Val Phe Gly Gly Gly Thr Lys Leu Thr Val Leu
            100                 105                 110

<210> SEQ ID NO 9
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-TIM-3 antibody clone 2C8

<400> SEQUENCE: 9

Gln Ser Val Leu Thr Gln Pro Pro Ser Val Ser Ala Ala Pro Gly Gln
1               5                   10                  15

```
Lys Val Thr Ile Ser Cys Ser Gly Ser Ser Asn Ile Gly Asn Asn
             20                  25                  30

Tyr Val Ser Trp Tyr Gln Gln Leu Pro Gly Thr Ala Pro Lys Leu Leu
             35                  40                  45

Ile Tyr Gly Asn Asn Trp Arg Pro Ser Gly Ile Pro Asp Arg Phe Ser
     50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Ser Trp Asp Ala Ala
                 85                  90                  95

Ala Ala Gly Tyr Phe Gly Gly Gly Thr Lys Leu Thr Val Leu
            100                 105                 110

<210> SEQ ID NO 10
<211> LENGTH: 13
<212> TYPE: PRT
<213> ORGANISM: Artificial sequence
<220> FEATURE:
<223> OTHER INFORMATION: Synthetic sequence: LC-CDR1

<400> SEQUENCE: 10

Ser Gly Ser Ser Ser Asn Ile Gly Asn Asn Tyr Val Ser
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic sequence: LC-CDR2

<400> SEQUENCE: 11

Gly Asn Asn Trp Arg Pro Ser
1               5

<210> SEQ ID NO 12
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 12

Glu Ala Trp Asp Tyr Tyr Val Ala Ala Gly Tyr
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 13

Asp Ser Trp Asp Ser Ala Asp Ala Ser Gly Val
1               5                   10

<210> SEQ ID NO 14
<211> LENGTH: 11
<212> TYPE: PRT
<213> ORGANISM: Artificial sequence
<220> FEATURE:
<223> OTHER INFORMATION: Synthetic sequence: LC-CDR3
```

```
<400> SEQUENCE: 14

Asp Ser Trp Asp Tyr Asp Tyr Ala Ala Gly Val
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 15

Asp Ser Trp Asp Ser Tyr Leu Ala Ala Gly Val
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 16

Glu Ser Trp Asp Tyr Asp Tyr Ala Ser Gly Val
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 17

Asp Ser Trp Asp Ser Ser Asp Ser Ser Gly Val
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 18

Glu Ala Trp Asp Ser Ala Tyr Ala Ala Gly Ser
1               5                   10

<210> SEQ ID NO 19
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 19

Asp Ser Trp Asp Ala Ala Leu Ser Ala Gly Val
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 20
```

Glu Ser Trp Asp Ala Ala Ala Ala Gly Tyr
1               5                   10

<210> SEQ ID NO 21
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 1B9

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Ser Asp Ala Trp Gly Gln Gly Thr Leu Val
            100                 105                 110

Thr Val Ser Ser
        115

<210> SEQ ID NO 22
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 1H9

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Phe Asp Asp Trp Gly Gln Gly Thr Leu Val
            100                 105                 110

Thr Val Ser Ser
        115

<210> SEQ ID NO 23
<211> LENGTH: 116
<212> TYPE: PRT
<213> ORGANISM: Artificial sequence

```
<220> FEATURE:
<223> OTHER INFORMATION: Synthetic sequence: Heavy chain variable domain
      sequence for anti-TIM-3 antibody clone 1H10

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Phe Asp Ser Trp Gly Gln Gly Thr Leu Val
            100                 105                 110

Thr Val Ser Ser
        115

<210> SEQ ID NO 24
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 2C7

<400> SEQUENCE: 24

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Tyr Asp Tyr Trp Gly Gln Gly Thr Leu Val
            100                 105                 110

Thr Val Ser Ser
        115

<210> SEQ ID NO 25
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 2F4

<400> SEQUENCE: 25

Gln Val Gln Leu Gln Gln Trp Gly Ala Gly Leu Leu Lys Pro Ser Glu
1               5                   10                  15
```

-continued

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Ser Asp Ala Trp Gly Gln Gly Thr Leu Val
                100                 105                 110

Thr Val Ser Ser
        115

<210> SEQ ID NO 26
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 2G6

<400> SEQUENCE: 26

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Val Ala Gly Phe Asp Ser Trp Gly Gln Gly Thr Leu Val
                100                 105                 110

Thr Val Ser Ser
        115

<210> SEQ ID NO 27
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 1D9

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Tyr Ala Gly Asp Asp Tyr Trp Gly Gln Gly Thr Leu Val
                100                 105                 110

Thr Val Ser Ser
        115

<210> SEQ ID NO 28
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 1F4

<400> SEQUENCE: 28

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Val Ala Gly Tyr Asp Tyr Trp Gly Gln Gly Thr Leu Val
                100                 105                 110

Thr Val Ser Ser
        115

<210> SEQ ID NO 29
<211> LENGTH: 116
<212> TYPE: PRT
<213> ORGANISM: Artificial sequence
<220> FEATURE:
<223> OTHER INFORMATION: Synthetic sequence: Heavy chain variable domain
      sequence for anti-TIM-3 antibody clone 2C8

<400> SEQUENCE: 29

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Val Ala Gly Ser Asp Ala Trp Gly Gln Gly Thr Leu Val
                100                 105                 110
```

Thr Val Ser Ser
        115

<210> SEQ ID NO 30
<211> LENGTH: 10
<212> TYPE: PRT
<213> ORGANISM: Artificial sequence
<220> FEATURE:
<223> OTHER INFORMATION: Synthetic sequence: HC-CDR1

<400> SEQUENCE: 30

Gly Gly Ser Phe Ser Gly Tyr Tyr Trp Ser
1               5                   10

<210> SEQ ID NO 31
<211> LENGTH: 16
<212> TYPE: PRT
<213> ORGANISM: Artificial sequence
<220> FEATURE:
<223> OTHER INFORMATION: Synthetic sequence: HC-CDR2

<400> SEQUENCE: 31

Glu Ile Asn His Ser Gly Ser Thr Asn Tyr Asn Pro Ser Leu Lys Ser
1               5                   10                  15

<210> SEQ ID NO 32
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 32

Gly Tyr Val Ala Gly Ser Asp Ala
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 33

Gly Tyr Val Ala Gly Phe Asp Asp
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 34

Gly Tyr Val Ala Gly Phe Asp Ser
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 35

Gly Tyr Val Ala Gly Tyr Asp Tyr

<210> SEQ ID NO 36
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 36

Gly Tyr Val Ala Gly Ser Asp Ala
1               5

<210> SEQ ID NO 37
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 37

Gly Tyr Val Ala Gly Phe Asp Ser
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 38

Gly Tyr Tyr Ala Gly Asp Asp Tyr
1               5

<210> SEQ ID NO 39
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 39

Gly Tyr Val Ala Gly Tyr Asp Tyr
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic sequence: HC-CDR3

<400> SEQUENCE: 40

Gly Tyr Val Ala Gly Ser Asp Ala
1               5

<210> SEQ ID NO 41
<211> LENGTH: 11
<212> TYPE: PRT
<213> ORGANISM: Artificial sequence
<220> FEATURE:
<223> OTHER INFORMATION: Synthetic sequence: LC-CDR3
<220> FEATURE:
<221> NAME/KEY: VARIANT
<222> LOCATION: (1)..(1)
<223> OTHER INFORMATION: Xaa = Glu or Asp
<220> FEATURE:

```
<221> NAME/KEY: VARIANT
<222> LOCATION: (2)..(2)
<223> OTHER INFORMATION: Xaa = Ala or Ser
<220> FEATURE:
<221> NAME/KEY: VARIANT
<222> LOCATION: (5)..(5)
<223> OTHER INFORMATION: Xaa = Tyr, Ser or Ala
<220> FEATURE:
<221> NAME/KEY: VARIANT
<222> LOCATION: (6)..(6)
<223> OTHER INFORMATION: Xaa = Tyr, Ala, Asp or Ser
<220> FEATURE:
<221> NAME/KEY: VARIANT
<222> LOCATION: (7)..(7)
<223> OTHER INFORMATION: Xaa = Val, Asp, Tyr, Leu or Ala
<220> FEATURE:
<221> NAME/KEY: VARIANT
<222> LOCATION: (8)..(8)
<223> OTHER INFORMATION: Xaa = Ala or Ser
<220> FEATURE:
<221> NAME/KEY: VARIANT
<222> LOCATION: (9)..(9)
<223> OTHER INFORMATION: Xaa = Ala or Ser
<220> FEATURE:
<221> NAME/KEY: VARIANT
<222> LOCATION: (11)..(11)
<223> OTHER INFORMATION: Xaa = Tyr, Val or Ser

<400> SEQUENCE: 41

Xaa Xaa Trp Asp Xaa Xaa Xaa Xaa Xaa Gly Xaa
 1               5                  10

<210> SEQ ID NO 42
<211> LENGTH: 8
<212> TYPE: PRT
<213> ORGANISM: Artificial sequence
<220> FEATURE:
<223> OTHER INFORMATION: Synthetic sequence: HC-CDR3
<220> FEATURE:
<221> NAME/KEY: VARIANT
<222> LOCATION: (3)..(3)
<223> OTHER INFORMATION: Xaa = Val or Tyr
<220> FEATURE:
<221> NAME/KEY: VARIANT
<222> LOCATION: (6)..(6)
<223> OTHER INFORMATION: Xaa = Ser, Phe, Tyr or Asp
<220> FEATURE:
<221> NAME/KEY: VARIANT
<222> LOCATION: (8)..(8)
<223> OTHER INFORMATION: Xaa = Ala, Asp, Ser or Tyr

<400> SEQUENCE: 42

Gly Tyr Xaa Ala Gly Xaa Asp Xaa
 1               5

<210> SEQ ID NO 43
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      1B9

<400> SEQUENCE: 43
cagtctgtgt tgacgcagcc gccctcagtg tctgcggccc caggacagaa agtcaccatc        60
tcctgctctg gaagcagctc caacattggg aataattatg tatcctggta ccagcagctc       120
ccaggaacag cccccaaact cctcatttat ggcaataatt ggcgaccctc agggattcct       180
gaccgcttct ctggctccaa gtctggcacc tcagccaccc tgggcatcac cggacttcag       240
actggggacg aggccgatta ttactgcgaa gcttgggatt attatgttgc tgctgggtat       300
```
ttcggcggag ggaccaagct gaccgtccta            330

<210> SEQ ID NO 44
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      1H9

<400> SEQUENCE: 44
cagtctgtgc tgacgcagcc gccctcagtg tctgcggccc caggacagaa agtcaccatc            60
tcctgctctg gaagcagctc caacattggg aataattatg tatcctggta ccagcagctc           120
ccaggaacag ccccccaaact cctcatttat ggcaataatt ggcgaccctc agggattcct          180
gaccgcttct ctggctccaa gtctggcacc tcagccaccc tgggcatcac cggacttcag          240
actggggacg aggccgatta ttactgcgat tcttgggatt ctgctgatgc ttctggggtt          300
ttcggcggag ggaccaagct gaccgtccta            330

<210> SEQ ID NO 45
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      1H10

<400> SEQUENCE: 45
cagtctgtgc tgacgcagcc gccctcagtg tctgcggccc caggacagaa agtcaccatc            60
tcctgctctg gaagcagctc caacattggg aataattatg tatcctggta ccagcagctc           120
ccaggaacag ccccccaaact cctcatttat ggcaataatt ggcgaccctc agggattcct          180
gaccgcttct ctggctccaa gtctggcacc tcagccaccc tgggcatcac cggacttcag          240
actggggacg aggccgatta ttactgcgat tcttgggatt atgattatgc tgctggggtt          300
ttcggcggag ggaccaagct gaccgtccta            330

<210> SEQ ID NO 46
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      2C7

<400> SEQUENCE: 46
cagtctgtgt tgacgcagcc gccctcagtg tctgcggccc caggacagaa agtcaccatc            60
tcctgctctg gaagcagctc caacattggg aataattatg tatcctggta ccagcagctc           120
ccaggaacag ccccccaaact cctcatttat ggcaataatt ggcgaccctc agggattcct          180
gaccgcttct ctggctccaa gtctggcacc tcagccaccc tgggcatcac cggacttcag          240
actggggacg aggccgatta ttactgcgat tcttgggatt cttatcttgc tgctggggtt          300
ttcggcggag ggaccaagct gaccgtccta            330

<210> SEQ ID NO 47
<211> LENGTH: 330
<212> TYPE: DNA

```
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      2F4

<400> SEQUENCE: 47
cagtctgtgc tgacgcagcc gccctcagtg tctgcggccc caggacagaa agtcaccatc        60
tcctgctctg gaagcagctc caacattggg aataattatg tatcctggta ccagcagctc       120
ccaggaacag cccccaaact cctcatttat ggcaataatt ggcgaccctc agggattcct       180
gaccgcttct ctggctccaa gtctggcacc tcagccaccc tgggcatcac cggacttcag       240
actggggacg aggccgatta ttactgcgaa tcttgggatt atgattatgc ttctggggtt       300
ttcggcggag ggaccaagct gaccgtccta                                         330

<210> SEQ ID NO 48
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      2G6

<400> SEQUENCE: 48
cagtctgtgt tgacgcagcc gccctcagtg tctgcggccc caggacagaa agtcaccatc        60
tcctgctctg gaagcagctc caacattggg aataattatg tatcctggta ccagcagctc       120
ccaggaacag cccccaaact cctcatttat ggcaataatt ggcgaccctc agggattcct       180
gaccgcttct ctggctccaa gtctggcacc tcagccaccc tgggcatcac cggacttcag       240
actggggacg aggccgatta ttactgcgat tcttgggatt cttctgattc ttctggggtt       300
ttcggcggag ggaccaagct gaccgtccta                                         330

<210> SEQ ID NO 49
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      1D9

<400> SEQUENCE: 49
cagtctgtgc tgacgcagcc gccctcagtg tctgcggccc caggacagaa agtcaccatc        60
tcctgctctg gaagcagctc caacattggg aataattatg tatcctggta ccagcagctc       120
ccaggaacag cccccaaact cctcatttat ggcaataatt ggcgaccctc agggattcct       180
gaccgcttct ctggctccaa gtctggcacc tcagccaccc tgggcatcac cggacttcag       240
actggggacg aggccgatta ttactgcgaa gcttgggatt ctgcttatgc tgctgggtct       300
ttcggcggag ggaccaagct gaccgtccta                                         330

<210> SEQ ID NO 50
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      1F4

<400> SEQUENCE: 50
```

```
cagtctgtgt tgacgcagcc gccctcagtg tctgcggccc caggacagaa agtcaccatc    60
tcctgctctg gaagcagctc caacattggg aataattatg tatcctggta ccagcagctc   120
ccaggaacag cccccaaact cctcatttat ggcaataatt ggcgaccctc agggattcct   180
gaccgcttct ctggctccaa gtctggcacc tcagccaccc tgggcatcac cggacttcag   240
actggggacg aggccgatta ttactgcgat tcttgggatg ctgctctttc tgctggggtt   300
ttcggcggag ggaccaagct gaccgtccta                                    330
```

<210> SEQ ID NO 51
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-TIM-3 antibody clone
      2C8

<400> SEQUENCE: 51

```
cagtctgtgc tgacgcagcc gccctcagtg tctgcggccc caggacagaa agtcaccatc    60
tcctgctctg gaagcagctc caacattggg aataattatg tatcctggta ccagcagctc   120
ccaggaacag cccccaaact cctcatttat ggcaataatt ggcgaccctc agggattcct   180
gaccgcttct ctggctccaa gtctggcacc tcagccaccc tgggcatcac cggacttcag   240
actggggacg aggccgatta ttactgcgaa tcttgggatg ctgctgctgc tgctgggtat   300
ttcggcggag ggaccaagct gaccgtccta                                    330
```

<210> SEQ ID NO 52
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      1B9

<400> SEQUENCE: 52

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca gagtcgagt caccatatca gtagacacgt ccaagaacca gttctccttg    240
aaactgagct ctgtgaccgc cgcggacacg gctgtgtatt actgtgcgag aggctatgtt   300
gctggctctg atgcttgggg ccagggaacc ctggtcaccg tctcaagc                348
```

<210> SEQ ID NO 53
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      1H9

<400> SEQUENCE: 53

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
```

```
ccgtccctca agagtcgagt caccatatca gtagacacgt ccaagaacca gttctccttg      240
aaactgagct ctgtgaccgc cgcggacacg gctgtgtatt actgtgcgag aggctatgtt      300
gctggctttg atgattgggg ccagggaacc ctggtcaccg tctcaagc                   348
```

<210> SEQ ID NO 54
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      1H10

<400> SEQUENCE: 54

```
caggtgcagc tacagcagtg gggcgcagga ctgttgaagc cttcggagac cctgtccctc      60
acctgcgctg tctatggtgg gtccttcagt ggttactact ggagctggat ccgccagccc      120
ccagggaagg ggctggagtg gattggggaa atcaatcata gtggaagcac caactacaac      180
ccgtccctca agagtcgagt caccatatca gtagacacgt ccaagaacca gttctccttg      240
aaactgagct ctgtgaccgc cgcggacacg gctgtgtatt actgtgcgag aggctatgtt      300
gctggctttg attcttgggg ccagggaacc ctggtcaccg tctcaagc                   348
```

<210> SEQ ID NO 55
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      2C7

<400> SEQUENCE: 55

```
caggtgcagc tacagcagtg gggcgcagga ctgttgaagc cttcggagac cctgtccctc      60
acctgcgctg tctatggtgg gtccttcagt ggttactact ggagctggat ccgccagccc      120
ccagggaagg ggctggagtg gattggggaa atcaatcata gtggaagcac caactacaac      180
ccgtccctca agagtcgagt caccatatca gtagacacgt ccaagaacca gttctccttg      240
aaactgagct ctgtgaccgc cgcggacacg gctgtgtatt actgtgcgag aggctatgtt      300
gctggctatg attattgggg ccagggaacc ctggtcaccg tctcaagc                   348
```

<210> SEQ ID NO 56
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      2F4

<400> SEQUENCE: 56

```
caggtgcagc tacagcagtg gggcgcagga ctgttgaagc cttcggagac cctgtccctc      60
acctgcgctg tctatggtgg gtccttcagt ggttactact ggagctggat ccgccagccc      120
ccagggaagg ggctggagtg gattggggaa atcaatcata gtggaagcac caactacaac      180
ccgtccctca agagtcgagt caccatatca gtagacacgt ccaagaacca gttctccttg      240
aaactgagct ctgtgaccgc cgcggacacg gctgtgtatt actgtgcgag aggctatgtt      300
gctggctctg atgcttgggg ccagggaacc ctggtcaccg tctcaagc                   348
```

```
<210> SEQ ID NO 57
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      2G6

<400> SEQUENCE: 57
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccttg     240
aaactgagct ctgtgaccgc cgcggacacg gctgtgtatt actgtgcgag aggctatgtt     300
gctggctttg attcttgggg ccagggaacc ctggtcaccg tctcaagc                  348

<210> SEQ ID NO 58
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      1D9

<400> SEQUENCE: 58
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccttg     240
aaactgagct ctgtgaccgc cgcggacacg gctgtgtatt actgtgcgag aggctattat     300
gctggcgatg attattgggg ccagggaacc ctggtcaccg tctcaagc                  348

<210> SEQ ID NO 59
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
      1F4

<400> SEQUENCE: 59
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccttg     240
aaactgagct ctgtgaccgc cgcggacacg gctgtgtatt actgtgcgag aggctatgtt     300
gctggctatg attattgggg ccagggaacc ctggtcaccg tctcaagc                  348

<210> SEQ ID NO 60
<211> LENGTH: 348
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-TIM-3 antibody clone
```

2C8

<400> SEQUENCE: 60

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccttg   240
aaactgagct ctgtgaccgc cgcggacacg gctgtgtatt actgtgcgag aggctatgtt   300
gctggctctg atgcttgggg ccagggaacc ctggtcaccg tctcaagc                348
```

<210> SEQ ID NO 61
<211> LENGTH: 5
<212> TYPE: PRT
<213> ORGANISM: Artificial sequence
<220> FEATURE:
<223> OTHER INFORMATION: Synthetic sequence: HC-CDR1

<400> SEQUENCE: 61

```
Gly Tyr Tyr Trp Ser
1               5
```

ANTI-TIM-3 ANTIBODIES

RELATED APPLICATIONS

This application is a 35 U.S.C. § 371 national phase application of PCT/SG2015/050414 (WO 2016/068802), filed Oct. 27, 2015, entitled "Anti-TIM-3 Antibodies". International application serial no. PCT/SG2015/050414 claims priority to GB application serial no. 1419094.6, filed Oct. 27, 2014. Each of the above-referenced applications are incorporated herein by reference in their entirety.

REFERENCE TO A "SEQUENCE LISTING"

Incorporated by reference herein in its entirety is the Sequence Listing entitled "sequence Listing.txt", created Apr. 23, 2017, size of 39 kilobytes.

FIELD OF THE INVENTION

The present invention relates to antibodies that bind to T cell immunoglobulin mucin 3 (TIM-3).

BACKGROUND TO THE INVENTION

T-cell exhaustion is a state of T-cell dysfunction that arises during many chronic infections and cancer. It is defined by poor T-cell effector function, sustained expression of inhibitory receptors and a transcriptional state distinct from that of functional effector or memory T-cells. Exhaustion prevents optimal control of infection and tumors. (E John Wherry., *Nature Immunology* 12, 492-499 (2011)).

T-cell exhaustion is characterized by the stepwise and progressive loss of T-cell functions. Exhaustion is well-defined during chronic lymphocytic choriomeningitis virus infection and commonly develops under conditions of antigen-persistence, which occur following many chronic infections including hepatitis B virus, hepatitis C virus and human immunodeficiency virus infections, as well as during tumor metastasis. Exhaustion is not a uniformly disabled setting as a gradation of phenotypic and functional defects can manifest, and these cells are distinct from prototypic effector, memory and also anergic T cells. Exhausted T cells most commonly emerge during high-grade chronic infections, and the levels and duration of antigenic stimulation are critical determinants of the process. (Yi et al., *Immunology* April 2010; 129(4):474-481).

Circulating human tumor-specific CD8$^+$ T cells may be cytotoxic and produce cytokines in vivo, indicating that self- and tumor-specific human CD8$^+$ T cells can reach functional competence after potent immunotherapy such as vaccination with peptide, incomplete Freund's adjuvant (IFA), and CpG or after adoptive transfer. In contrast to peripheral blood, T-cells from metastasis are functionally deficient, with abnormally low cytokine production and upregulation of the inhibitory receptors PD-1, CTLA-4, and TIM-3.

Functional deficiency is reversible, since T-cells isolated from melanoma tissue can restore IFN-γ production after short-term in vitro culture. However, it remains to be determined whether this functional impairment involves further molecular pathways, possibly resembling T-cell exhaustion or anergy as defined in animal models. (Baitsch et al., *J Clin Invest.* 2011; 121(6):2350-2360).

Programmed cell death 1 (PD-1), also called CD279, is a type I membrane protein encoded in humans by the PDCD1 gene. It has two ligands, PD-L1 and PD-L2.

The PD-1 pathway is a key immune-inhibitory mediator of T-cell exhaustion. Blockade of this pathway can lead to T-cell activation, expansion, and enhanced effector functions. As such, PD-1 negatively regulates T cell responses. PD-1 has been identified as a marker of exhausted T cells in chronic disease states, and blockade of PD-1:PD-1L interactions has been shown to partially restore T cell function. (Sakuishi et al., *JEM* Vol. 207, Sep. 27, 2010, pp 2187-2194).

Nivolumab (BMS-936558) is an anti-PD-1 antibody that was approved for the treatment of melanoma in Japan in July 2014. Other anti-PD-1 antibodies are described in WO 2010/077634, WO 2006/121168.

T cell immunoglobulin mucin 3 (TIM-3) is an immune regulator identified as being upregulated on exhausted CD8$^+$ T cells (Sakuishi et al., *JEM* Vol. 207, Sep. 27, 2010, pp 2187-2194). TIM-3 was originally identified as being selectively expressed on IFN-γ-secreting Th1 and Tc1 cells. Interaction of TIM-3 with its ligand, galectin-9, triggers cell death in TIM-3$^+$ T cells. Anti-TIM-3 antibodies are described in Ngiow et al (*Cancer Res.* 2011 May 15; 71(10):3540-51), and in U.S. Pat. No. 8,552,156

Both TIM-3 and PD-1 can function as negative regulators of T cell responses and combined targeting of the TIM-3 and PD-1 pathways is more effective in controlling tumor growth than targeting either pathway alone. (Sakuishi et al., *JEM* Vol. 207, Sep. 27, 2010, pp 2187-2194; and Ngiow et al *Cancer Res.* 2011 May 15; 71 (10):3540-51).

TIM-3 can also be expressed on the surface of tumor cells, particularly tumor cells of hematopoietic origin, such for example acute myeloid leukemia cells (Kikushige et al., Cell Stem Cell 2010; 3:7(6)708-17), Therefore in some instances TIM-3 could be a tumor-associated antigen that could be targeted by specific antibodies.

SUMMARY OF THE INVENTION

The present invention is concerned with antibodies, or antigen binding fragments, that bind to TIM-3. Heavy and light chain polypeptides are also disclosed. The antibodies, antigen binding fragments and polypeptides may be provided in isolated and/or purified form and may be formulated into compositions suitable for use in research, therapy and diagnosis.

In some embodiments the antibody, or antigen binding fragment, or polypeptide is cytotoxic, e.g. against TIM-3 expressing cells, such as TIM-3 expressing T-cells or tumor cells. In some embodiments the antibody, or antigen binding fragment, or polypeptide is useful in treating cancer owing to its cytotoxic effect. Suitable cancers include leukemia, such as acute myeloid leukemia.

In some embodiments the antibody, or antigen binding fragment, or polypeptide may be effective to restore T-cell function in T-cells, e.g. CD8$^+$ T-cells, exhibiting T-cell exhaustion or T-cell anergy.

In one aspect of the present invention an antibody, or antigen binding fragment, is provided, the amino acid sequence of the antibody may comprise the amino acid sequences i) to iii), or the amino acid sequences iv) to vi), or preferably the amino acid sequences i) to vi):

i) LC-CDR1:

SGSSSNIGNNYVS (SEQ ID NO: 10)

-continued ii) LC-CDR2:
GNNWRPS (SEQ ID NO: 11)

iii) LC-CDR3:
$X_1X_2WDX_3X_4X_5X_6X_7GX_8$ (SEQ ID NO: 41)

iv) HC-CDR1:
GGSFSGYYWS, (SEQ ID NO: 30)
or
GYYWS (SEQ ID NO: 61)

v) HC-CDR2:
EINHSGSTNYNPSLKS (SEQ ID NO: 31)

vi) HC-CDR3:
$GYZ_1AGZ_2DZ_3$ (SEQ ID NO: 42)

or a variant thereof in which one or two or three amino acids in one or more of the sequences (i) to (vi) are replaced with another amino acid, where $X_1$=E or D, $X_2$=A or S, $X_3$=Y, S or A, $X_4$=Y, A, D or S, $X_5$=V, D, Y, L or A, $X_6$=A or S, $X_7$=A or S, $X_8$=Y, V or S and $Z_1$=V or Y, $Z_2$=S, F, Y or D, $Z_3$=A, D, S or Y.

In connection with all aspects of the present invention, in embodiments wherein HC-CDR1: GYYWS (SEQ ID NO:61), this sequence may be comprised in the larger sequence GGSFSGYYWS (SEQ ID NO:30).

In some embodiments, LC-CDR3 is one of EAWDYY-VAAGY (SEQ ID NO:12), DSWDSADASGV (SEQ ID NO:13), DSWDYDYAAGV (SEQ ID NO:14), DSWDSY-LAAGV (SEQ ID NO:15), ESWDYDYASGV (SEQ ID NO:16), DSWDSSDSSGV (SEQ ID NO:17), EAWD-SAYAAGS(SEQ ID NO:18) DSWDAALSAGV (SEQ ID NO:19) or ESWDAAAAAGY (SEQ ID NO:20).

In some embodiments HC-CDR3 is one of GYVAGSDA (SEQ ID NO:32), GYVAGFDD (SEQ ID NO:33), GYVAGFDS (SEQ ID NO:34), GYVAGYDY (SEQ ID NO:35), GYVAGSDA (SEQ ID NO:36), GYVAGFDS (SEQ ID NO:37), GYYAGDDY (SEQ ID NO:38), GYVAGYDY (SEQ ID NO:39), or GYVAGSDA (SEQ ID NO:40).

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

LC-CDR3:
EAWDYYVAAGY (SEQ ID NO: 12)

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

LC-CDR3:
DSWDSADASGV (SEQ ID NO: 13)

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

LC-CDR3:
DSWDYDYAAGV (SEQ ID NO: 14)

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

LC-CDR3:
DSWDSYLAAGV (SEQ ID NO: 15)

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

LC-CDR3:
ESWDYDYASGV (SEQ ID NO: 16)

In some embodiments the antibody, or antigen binding fragment, may comprise at least one light chain variable region incorporating the following CDRs:

LC-CDR1:
SGSSSNIGNNYVS (SEQ ID NO: 10)

LC-CDR2:
GNNWRPS (SEQ ID NO: 11)

-continued

LC-CDR3:
(SEQ ID NO: 17)
DSWDSSDSSGV

In some embodiments the antibody, or antigen binding fragment, may comprise at least one light chain variable region incorporating the following CDRs:

LC-CDR1:
(SEQ ID NO: 10)
SGSSSNIGNNYV

LC-CDR2:
(SEQ ID NO: 11)
GNNWRPS

LC-CDR3:
(SEQ ID NO: 18)
EAWDSAYAAGS

In some embodiments the antibody, or antigen binding fragment, may comprise at least one light chain variable region incorporating the following CDRs:

LC-CDR1:
(SEQ ID NO: 10)
SGSSSNIGNNYVS

LC-CDR2:
(SEQ ID NO: 11)
GNNWRPS

LC-CDR3:
(SEQ ID NO: 19)
DSWDAALSAGV

In some embodiments the antibody, or antigen binding fragment, may comprise at least one light chain variable region incorporating the following CDRs:

LC-CDR1:
(SEQ ID NO: 10)
SGSSSNIGNNYVS

LC-CDR2:
(SEQ ID NO: 11)
GNNWRPS

LC-CDR3:
(SEQ ID NO: 20)
ESWDAAAAGY

In some embodiments the antibody, or antigen binding fragment, may comprise at least one heavy chain variable region incorporating the following CDRs:

HC-CDR1:
(SEQ ID NO: 30)
GGSFSGYYWS,
or
(SEQ ID NO: 61)
GYYWS

HC-CDR2:
(SEQ ID NO: 31)
EINHSGSTNYNPSLKS

HC-CDR3:
(SEQ ID NO: 32)
GYVAGSDA

In some embodiments the antibody, or antigen binding fragment, may comprise at least one heavy chain variable region incorporating the following CDRs:

HC-CDR1:
(SEQ ID NO: 30)
GGSFSGYYWS,
or
(SEQ ID NO: 61)
GYYWS

HC-CDR2:
(SEQ ID NO: 31)
EINHSGSTNYNPSLKS

HC-CDR3:
(SEQ ID NO: 33)
GYVAGFDD

In some embodiments the antibody, or antigen binding fragment, may comprise at least one heavy chain variable region incorporating the following CDRs:

In some embodiments the antibody, or antigen binding fragment, may comprise at least one heavy chain variable region incorporating the following CDRs:

HC-CDR1:
(SEQ ID NO: 30)
GGSFSGYYWS,
or
(SEQ ID NO: 61)
GYYWS

HC-CDR2:
(SEQ ID NO: 31)
EINHSGSTNYNPSLKS

HC-CDR3:
(SEQ ID NO: 34)
GYVAGFDS

In some embodiments the antibody, or antigen binding fragment, may comprise at least one heavy chain variable region incorporating the following CDRs:

HC-CDR1:
(SEQ ID NO: 30)
GGSFSGYYWS,
or
(SEQ ID NO: 61)
GYYWS

HC-CDR2:
(SEQ ID NO: 31)
EINHSGSTNYNPSLKS

HC-CDR3:
(SEQ ID NO: 35)
GYVAGYDY

In some embodiments the antibody, or antigen binding fragment, may comprise at least one heavy chain variable region incorporating the following CDRs:

```
HC-CDR1:
                              (SEQ ID NO: 30)
GGSFSGYYWS,
or (SEQ ID NO: 61)
GYYWS

HC-CDR2:
                              (SEQ ID NO: 31)
EINHSGSTNYNPSLKS

HC-CDR3:
                              (SEQ ID NO: 36)
GYVAGSDA
```

In some embodiments the antibody, or antigen binding fragment, may comprise at least one heavy chain variable region incorporating the following CDRs:

```
HC-CDR1:
                              (SEQ ID NO: 30)
GGSFSGYYWS,
or (SEQ ID NO: 61)
GYYWS

HC-CDR2:
                              (SEQ ID NO: 31)
EINHSGSTNYNPSLKS

HC-CDR3:
                              (SEQ ID NO: 37)
GYVAGFDS
```

In some embodiments the antibody, or antigen binding fragment, may comprise at least one heavy chain variable region incorporating the following CDRs:

```
HC-CDR1:
                              (SEQ ID NO: 30)
GGSFSGYYWS,
or (SEQ ID NO: 61)
GYYWS

HC-CDR2:
                              (SEQ ID NO: 31)
EINHSGSTNYNPSLKS

HC-CDR3:
                              (SEQ ID NO: 38)
GYYAGDDY
```

In some embodiments the antibody, or antigen binding fragment, may comprise at least one heavy chain variable region incorporating the following CDRs:

```
HC-CDR1:
                              (SEQ ID NO: 30)
GGSFSGYYWS,
or (SEQ ID NO: 61)
GYYWS

HC-CDR2:
                              (SEQ ID NO: 31)
EINHSGSTNYNPSLKS

HC-CDR3:
                              (SEQ ID NO: 39)
GYVAGYDY
```

In some embodiments the antibody, or antigen binding fragment, may comprise at least one heavy chain variable region incorporating the following CDRs:

```
HC-CDR1:
                              (SEQ ID NO: 30)
GGSFSGYYWS,
or (SEQ ID NO: 61)
GYYWS

HC-CDR2:
                              (SEQ ID NO: 31)
EINHSGSTNYNPSLKS

HC-CDR3:
                              (SEQ ID NO: 40)
GYVAGSDA
```

The antibody may comprise at least one light chain variable region incorporating the CDRs shown in FIG. 1 or 2. The antibody may comprise at least one heavy chain variable region incorporating the CDRs shown in FIG. 1 or 3.

The antibody may comprise at least one light chain variable region ($V_L$) comprising the amino acid sequence of one of SEQ ID NOs 1, 10, 11, 12 or 2, 10, 11, 13 or 3, 10, 11, 14 or 4, 10, 11, 15 or 5, 10, 11, 16 or 6, 10, 11, 17 or 7, 10, 11, 18 or 8, 10, 11, 19 or 9, 10, 11, 20 or one of the amino acid sequences shown in FIG. 1 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 1, 10, 11, 12 or 2, 10, 11, 13 or 3, 10, 11, 14 or 4, 10, 11, 15 or 5, 10, 11, 16 or 6, 10, 11, 17 or 7, 10, 11, 18 or 8, 10, 11, 19 or 9, 10, 11, 20 or to the amino acid sequence of the $V_L$ chain amino acid sequence shown in FIG. 1.

The antibody may comprise at least one heavy chain variable region ($V_H$) comprising the amino acid sequence of one of SEQ ID NOs 21, 30 or 61, 31, 32 or 22, 30 or 61, 31, 33 or 23, 30 or 61, 31, 34 or 24, 30 or 61, 31, 35 or 25, 30 or 61, 31, 36 or 26, 30 or 61, 31, 37 or 27, 30 or 61, 31, 38 or 28, 30 or 61, 31, 39 or 29, 30 or 61, 31, 40 or one of the amino acid sequences shown in FIG. 2 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 21, 30 or 61, 31, 32 or 22, 30 or 61, 31, 33 or 23, 30 or 61, 31, 34 or 24, 30 or 61, 31, 35 or 25, 30 or 61, 31, 36 or 26, 30 or 61, 31, 37 or 27, 30 or 61, 31, 38 or 28, 30 or 61, 31, 39 or 29, 30 or 61, 31, 40 or to the amino acid sequence of the $V_H$ chain amino acid sequence shown in FIG. 2.

The antibody may comprise at least one light chain variable region comprising the amino acid sequence of one of SEQ ID NOs 1, 10, 11, 12 or 2, 10, 11, 13 or 3, 10, 11, 14 or 4, 10, 11, 15 or 5, 10, 11, 16 or 6, 10, 11, 17 or 7, 10, 11, 18 or 8, 10, 11, 19 or 9, 10, 11, 20 or one of the amino acid sequences shown in FIG. 1 (or an amino acid sequence having at least 70%, more preferably one of at least 75%, 80%, 85%, 90%, 95%, 96%, 97%, 98%, 99% or 100%, sequence identity to one of SEQ ID NOs 1, 10, 11, 12 or 2, 10, 11, 13 or 3, 10, 11, 14 or 4, 10, 11, 15 or 5, 10, 11, 16 or 6, 10, 11, 17 or 7, 10, 11, 18 or 8, 10, 11, 19 or 9, 10, 11, 20 or to one of the amino acid sequences of the $V_L$ chain amino acid sequence shown in FIG. 1) and at least one heavy chain variable region comprising the amino acid sequence of one of SEQ ID NOs 21, 30 or 61, 31, 32 or 22, 30 or 61, 31, 33 or 23, 30 or 61, 31, 34 or 24, 30 or 61, 31, 35 or 25, 30 or 61, 31, 36 or 26, 30 or 61, 31, 37 or 27, 30 or 61, 31, 38 or 28, 30 or 61, 31, 39 or 29, 30 or 61, 31, 40 or one of the amino acid sequence shown in FIG. 2 (or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 21, 30 or 61, 31, 32 or 22, 30 or 61, 31, 33 or 23, 30 or 61, 31, 34 or 24, 30 or 61, 31, 35 or 25, 30 or 61, 31, 36 or 26, 30 or 61, 31, 37 or 27, 30 or 61, 31, 38 or 28, 30 or 61, 31, 39 or 29, 30 or 61, 31, 40 or to one of the amino acid sequences of the $V_H$ chain amino acid sequence shown in FIG. 2).

The antibody may optionally bind TIM-3. The antibody may optionally have amino acid sequence components as described above. The antibody may be an IgG. In one embodiment an in vitro complex, optionally isolated, comprising an antibody, or antigen binding fragment, as described herein, bound to TIM-3 is provided.

In one aspect of the present invention an isolated heavy chain variable region polypeptide is provided, the heavy chain variable region polypeptide comprising the following CDRs:

```
HC-CDR1:
                                       (SEQ ID NO: 30)
GGSFSGYYWS,
or (SEQ ID NO: 61)
GYYWS

HC-CDR2:
                                       (SEQ ID NO: 31)
EINHSGSTNYNPSLKS

HC-CDR3:
                                       (SEQ ID NO: 42)
GYZ₁AGZ₂DZ₃
``` where $Z_1$=V or Y, $Z_2$=S, F, Y or D, $Z_3$=A, D, S or Y.

In some embodiments HC-CDR3 is one of GYVAGSDA (SEQ ID NO:32), GYVAGFDD (SEQ ID NO:33), GYVAGFDS (SEQ ID NO:34), GYVAGYDY (SEQ ID NO:35), GYVAGSDA (SEQ ID NO:36), GYVAGFDS (SEQ ID NO:37), GYYAGDDY (SEQ ID NO:38), GYVAGYDY (SEQ ID NO:39), or GYVAGSDA (SEQ ID NO:40).

In one aspect of the present invention an antibody, or antigen binding fragment, is provided, the antibody, or antigen binding fragment, comprising a heavy chain and a light chain variable region sequence, wherein:
the heavy chain comprises a HC-CDR1, HC-CDR2, HC-CDR3, having at least 85% overall sequence identity to
HC-CDR1: GGSFSGYYWS (SEQ ID NO:30) or GYYWS (SEQ ID NO:61)
HC-CDR2: EINHSGSTNYNPSLKS (SEQ ID NO:31),
HC-CDR3: is one of
GYZ₁AGZ₂DZ₃ (SEQ ID NO:42), GYVAGSDA (SEQ ID NO:32), GYVAGFDD (SEQ ID NO:33), GYVAGFDS (SEQ ID NO:34), GYVAGYDY (SEQ ID NO:35), GYVAGSDA (SEQ ID NO:36), GYVAGFDS (SEQ ID NO:37), GYYAGDDY (SEQ ID NO:38), GYVAGYDY (SEQ ID NO:39), or GYVAGSDA (SEQ ID NO:40) respectively, where $Z_1$=V or Y, $Z_2$=S, F, Y, or D, $Z_3$=A, D, S or Y. and the light chain comprises a LC-CDR1, LC-CDR2, LC-CDR3, having at least 85% overall sequence identity to:
LC-CDR1: SGSSSNIGNNYVS (SEQ ID NO:10),
LC-CDR2: GNNWRPS (SEQ ID NO:11),
LC-CDR3: is one of
$X_1X_2WDX_3X_4X_5X_6X_7GX_8$ (SEQ ID NO:41),
EAWDYYVAAGY (SEQ ID NO:12),
DSWDSADASGV (SEQ ID NO:13), DSWDYDYAAGV (SEQ ID NO:14),
DSWDSYLAAGV (SEQ ID NO:15), ESWDYDYASGV (SEQ ID NO:16),
DSWDSSDSSGV (SEQ ID NO:17), EAWDSAYAAGS (SEQ ID NO:18),
DSWDAALSAGV (SEQ ID NO:19) or ESWDAAAAAGY (SEQ ID NO:20),
respectively, where $X_1$=E or D, $X_2$=A or S, $X_3$=Y, S or A, $X_4$=Y, A, D or S,
$X_5$=V, D, Y or L or A, $Xe_6$=A or S, $X_7$=A or S, $X_8$=Y, V or S.

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, or antigen binding fragment, optionally isolated, is provided comprising a heavy chain and a light chain variable region sequence, wherein:
the heavy chain sequence has at least 85% sequence identity to the heavy chain sequence of one of SEQ ID NOs: 21 to 29 (FIG. 2), and
the light chain sequence has at least 85% sequence identity to the light chain sequence of one of: SEQ ID NO:1 to 9 (FIG. 1).

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment, or polypeptide further comprises variable region heavy chain framework sequences between the CDRs according to the arrangement HCFR1:HC-CDR1:HCFR2:HC-CDR2:HCFR3:HC-CDR3:HCFR4. The framework sequences may be derived from human consensus framework sequences.

In one aspect of the present invention an isolated light chain variable region polypeptide, optionally in combination with a heavy chain variable region polypeptide as described herein, is provided, the light chain variable region polypeptide comprising the following CDRs:

```
LC-CDR1:
                                       (SEQ ID NO: 10)
SGSSSNIGNNYVS

LC-CDR2:
                                       (SEQ ID NO: 11)
GNNWRPS

LC-CDR3:
                                       (SEQ ID NO: 41)
X₁X₂WDX₃X₄X₅X₆X₇GX₈
``` where $X_1$=E or D, $X_2$=A or S, $X_3$=Y, S or A, $X_4$=Y, A, D or S, $X_5$=V, D, Y or L or A, $X_6$=A or S, $X_7$=A or S, $X_8$=Y, V or S.

In some embodiments, LC-CDR3 is one of EAWDYYVAAGY (SEQ ID NO:12), DSWDSADASGV (SEQ ID NO:13), DSWDYDYAAGV (SEQ ID NO:14), DSWDSYLAAGV (SEQ ID NO:15), ESWDYDYASGV (SEQ ID NO:16), DSWDSSDSSGV (SEQ ID NO:17), EAWD-SAYAAGS(SEQ ID NO:18) DSWDAALSAGV (SEQ ID NO:19) or ESWDAAAAAGY (SEQ ID NO:20).

In some embodiments the antibody, antigen binding fragment, or polypeptide further comprises variable region light chain framework sequences between the CDRs according to the arrangement LCFR1:LC-CDR1:LCFR2:LC-CDR2: LCFR3:LC-CDR3:LCFR4. The framework sequences may be derived from human consensus framework sequences.

In some embodiments, the antibody, or antibody binding fragment, may further comprise a human constant region. For example selected from one of IgG1, IgG2, IgG3 and IgG4.

In some embodiments, the antibody, or antibody binding fragment, may further comprise a murine constant region. For example, selected from one of IgG1, IgG2A, IgG2B and IgG3.

In another aspect of the present invention, an antibody or antigen binding fragment is provided, optionally isolated, which is capable of binding to TIM-3, and which is a bispecific antibody or a bispecific antigen binding fragment. In some embodiments, the bispecific antibody or bispecific antigen binding fragment comprises an antigen binding fragment or polypeptide capable of binding to TIM-3 as described herein, and additionally comprises an antigen binding domain which is capable of binding to another target protein, e.g. a target protein other than TIM-3. In some embodiments, the target protein is a cell surface receptor. In some embodiments, the target protein is a cell surface receptor expressed on the cell surface of immune cells, e.g. T cells. In some embodiments, the antigen binding domain capable of binding to another target protein may be capable of binding to a T cell receptor (TCR) complex or a component thereof. In some embodiments, the antigen binding domain may be capable of binding to CD3 or a CD3 polypeptide. In some embodiments, the antigen binding domain may be capable of binding to one or more of the CD3 polypeptides CD3γ, CD3δ, CD3ζ, or CD3ε. In some embodiments the bispecific antibody is a bispecific T-cell engager antibody. In some embodiments, the target protein may be a member of the CD28 family. In some embodiments, the member of the CD28 family is selected from PD-1, LAG3, ICOS, CTLA4, BTLA or CD28.

In another aspect of the present invention, a composition, e.g. a pharmaceutical composition or medicament, is provided. The composition may comprise an antibody, antigen binding fragment, or polypeptide as described herein and at least one pharmaceutically-acceptable carrier, excipient, adjuvant or diluent.

In another aspect of the present invention an isolated nucleic acid encoding an antibody, antigen binding fragment, or polypeptide as described herein is provided. The nucleic acid may have a sequence of one of SEQ ID NOs 43, 44, 45, 46, 47, 48, 49, 50, 51, 52, 53, 54, 55, 56, 57, 58, 59, 60 (FIG. 4), or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. E. coli.

In one aspect of the present invention a method for making an antibody, or antigen binding fragment or polypeptide as described herein is provided, the method comprising culturing a host cell as described herein under conditions suitable for the expression of a vector encoding the antibody, or antigen binding fragment or polypeptide, and recovering the antibody, or antigen binding fragment or polypeptide.

In another aspect of the present invention an antibody, antigen binding fragment or polypeptide is provided for use in therapy, or in a method of medical treatment. In another aspect of the present invention an antibody, antigen binding fragment or polypeptide as described herein is provided for use in the treatment of cancer or a T-cell dysfunctional disorder. In another aspect of the present invention, the use of an antibody, antigen binding fragment or polypeptide as described herein in the manufacture of a medicament or pharmaceutical composition for use in the treatment of cancer or a T-cell dysfunctional disorder is provided.

In another aspect a method, in vitro or in vivo, of killing a cell that expresses TIM-3 is provided, the method comprising administering an antibody, antigen binding fragment or polypeptide as described herein to a cell that expresses (or overexpresses) TIM-3. The cell may be a cancer cell, e.g. leukemia or acute myeloid leukemia cell, white blood cell or T-cell. In some embodiments, the acute myeloid leukemia cell may be a stem cell; for example, in some embodiments the acute myeloid leukemia cell may be CD34+.

In another aspect of the present invention a method of enhancing T-cell function comprising administering an antibody, antigen binding fragment or polypeptide as described herein to a dysfunctional T-cell is provided. The method may be performed in vitro or in vivo.

In another aspect of the present invention a method of treating cancer or a T-cell dysfunctional disorder is provided, the method comprising administering an antibody, antigen binding fragment or polypeptide as described herein to a patient suffering from cancer or a T-cell dysfunctional disorder.

In another aspect of the present invention a method of treating an infectious disease is provided, the method comprising administering an antibody, antigen binding fragment of polypeptide as described herein to a patient suffering from an infectious disease.

In another aspect of the present invention a method of modulating an immune response in a subject is provided, the method comprising administering to the subject an antibody, antigen binding fragment or polypeptide as described herein such that the immune response in the subject is modulated.

In another aspect of the present invention a method of inhibiting growth of tumor cells in a subject is provided, the method comprising administering to the subject a therapeutically effective amount of an antibody, antigen binding fragment or polypeptide as described herein.

In another aspect of the present invention a method is provided, the method comprising contacting a sample containing, or suspected to contain, TIM-3 with an antibody or antigen binding fragment, as described herein, and detecting the formation of a complex of antibody, or antigen binding fragment, and TIM-3.

In another aspect of the present invention a method of diagnosing a disease or condition in a subject is provided, the method comprising contacting, in vitro, a sample from the subject with an antibody, or antigen binding fragment, as described herein, and detecting the formation of a complex of antibody, or antigen binding fragment, and TIM-3.

In a further aspect of the present invention a method of selecting or stratifying a subject for treatment with a modulator of TIM-3 signalling is provided, the method comprising contacting, in vitro, a sample from the subject with an antibody, or antigen binding fragment, according to the present invention and detecting the formation of a complex of antibody, or antigen binding fragment, and TIM-3.

An aspect of the present invention is a method of selecting a patient for treatment with a modulator of TIM3 signalling, such as an anti-TIM3 antibody or anti-TIM3 agent, the method comprising contacting, in vitro, a sample from the subject with an antibody, or antigen binding fragment as described herein, and detecting the formation of a complex of the antibody, or antigen binding fragment, and TIM-3.

In a further aspect of the present invention the use of an antibody, or antigen binding fragment, as described herein, for the detection of TIM-3 in vitro is provided. In another aspect of the present invention the use of an antibody, or antigen binding fragment, as described herein, as an in vitro diagnostic agent is provided.

In a further aspect of the present invention a method for expanding a population of T cells is provided, wherein T cells are contacted in vitro or ex vive with an antibody, antigen binding fragment or polypeptide according to the present invention.

In a further aspect of the present invention a method of treatment of a subject having a T-cell dysfunctional disorder is provided, the method comprising culturing T cells obtained from a blood sample from a subject in the presence of an antibody, antigen binding fragment or polypeptide according to the present invention so as to expand the T cell population, collecting expanded T cells, and administering the expanded T cells to a subject in need of treatment.

In methods of the present invention the antibody, antigen binding fragment or polypeptide may be provided as a composition as described herein.

In some embodiments the antibody may be one of clones 1B9, 1H9, 1H10, 2C7, 2F4, 2G6, 1 D9, 1F4, 2C8.

DESCRIPTION

Antibodies

Antibodies according to the present invention preferably bind to TIM-3 (the antigen), preferably human or rhesus TIM-3, optionally with a Kd ($s^{-1}$) in the range $1.0 \times 10^{-6}$ to $4.0 \times 10^{-4}$.

In any aspect of the present invention the antibody preferably specifically binds TIM-3 (e.g. human or rhesus).

Antibodies according to the present invention may be provided in isolated form.

Antibodies according to the present invention may exhibit least one of the following properties:
 a) binds to human TIM-3 with a Kd of $1 \times 10^{-6}$ or less preferably one of $1 \times 10^{-5}$, $\leq 1 \times 10^{-4}$, or $\leq 1 \times 10^{-3}$;
 b) is cytotoxic against TIM-3 expressing cells (antibody dependent cell-mediated cytotoxicity, ADCC), e.g. TIM-3 expressing acute myeloid leukemia cells
 c) increases T-cell proliferation in a Mixed Lymphocyte Reaction (MLR) assay (e.g. see Bromelow et al *J. Immunol Methods,* 2001 Jan. 1; 247(1-2):1-8);
 d) increases interferon-gamma production in an MLR assay; or
 e) increases interleukin-2 (IL-2) secretion in an MLR assay.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies, such as Fab and $Fab_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to TIM-3 may also be made using phage display technology as is well known in the art.

Aspects of the present invention include bi-specific antibodies, e.g. composed of two different fragments of two different antibodies, such that the bi-specific antibody binds two types of antigen. One of the antigens is TIM-3, the bi-specific antibody comprising a fragment as described herein that binds to TIM-3. The antibody may contain a different fragment having affinity for a second antigen, which may be any desired antigen, for example CD3 which has been used in cancer immunotherapy to bind to cytotoxic cells, recruit and target them to the site of a tumor. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297. Baeuerle, P A et al., (2009 *Cancer Res* 69 (12): 4941-4944).

Accordingly, the present invention provides an antibody or antigen binding fragment which is capable of binding to TIM-3, and which is a bispecific antibody or a bispecific antigen binding fragment. In some embodiments, the bispecific antibody or bispecific antigen binding fragment may be isolated.

In some embodiments, the bispecific antibodies and bispecific antigen binding fragments comprise an antigen binding fragment or a polypeptide according to the present invention. In some embodiments, the bispecific antibodies and bispecific antigen binding fragments comprise an antigen binding domain capable of binding to TIM-3, wherein the antigen binding domain which is capable of binding to TIM-3 comprises or consists of an antigen binding fragment or a polypeptide according to the present invention.

In some embodiments the bispecific antibodies and bispecific antigen binding fragments comprise an antigen binding domain capable of binding to TIM-3, and an antigen binding domain capable of binding to another target protein.

The antigen binding domain capable of binding to another target protein may be capable of binding to another protein other than TIM-3. In some embodiments, the target protein is a cell surface receptor. In some embodiments, the target protein is a cell surface receptor expressed on the cell surface of immune cells. In some embodiments, the target protein is a cell surface receptor expressed on the cell surface of T cells.

In some embodiments, the antigen binding domain capable of binding to another target protein may be capable of binding to a T cell receptor (TCR) complex or a component thereof. In some embodiments, the antigen binding domain may be capable of binding to CD3 or a CD3 polypeptide. In some embodiments, the antigen binding domain may be capable of binding to one or more of the CD3 polypeptides CD3γ, CD3δ, CD3ζ, or CD3ε. In some embodiments the bispecific antibody is capable of directing T cell activity (e.g. cytotoxic activity) against a TIM-3 expressing cell. In some embodiments the bispecific antibody is a bispecific T-cell engager antibody. In some embodiments the bispecific antibody or fragment is capable of directing T cell activity (e.g. cytotoxic activity) against a TIM-3 expressing cell. That is, in some embodiments, T cell activity (e.g. cytotoxic activity) against a TIM-3 expressing cell is increased in the presence of the bispecific antibody or fragment (e.g. relative to activity against a TIM-3 expressing cell in the absence of the bispecific antibody or fragment). T cell activity against a TIM-3 expressing cell can be determined in vitro by methods well known to the skilled person, for example by incubating T cells with TIM-3 expressing cells and measuring cell lysis as described herein.

In some embodiments, the bispecific antibody is provided as a fusion protein of two single-chain variable fragments (scFV) format, comprising a $V_H$ and $V_L$ of a TIM-3 binding antibody or antibody fragment according to the present invention, and a $V_H$ and $V_L$ of an antibody or antibody fragment capable of binding to CD3 or a CD3 polypeptide.

In some embodiments, the antigen binding domain for CD3 or a CD3 polypeptide may comprise the CDRs, light and heavy chain variable domains or other CD3- or CD3 polypeptide-binding fragment of e.g. anti-CD3 antibody clone OKT3 (eBioscience), clone CD3-12 (AbD Serotec), clone UCHT1 (Southern Biotech) clone SP7 (Thermo Scientific Pierce Antibodies), clone SPV-T3b (Thermo Fisher Scientific), clone S4.1 (7D6) (Thermo Fisher Scientific), clone MEM-57 (AbD Serotec), clone 37895 (Miltenyi Biotec), clone CA-3 (Abcam), clone 4D10A6 (Abbiotec), clone HIT3a (Abbiotec), clone LT3 (Source BioScience), clone B-B11 (MyBioSource.com), clone 17A2 (Novus Biologicals), clone BC3 (BioLegend), clone HAM25-1352 (MBL International), clone CA-3 (Bosterbio), clone RBT-CD3 (Lifespan BioSciences), Ham25-1157 (Merck Millipore), clone CRIS-7 (Peninsula Laboratories International), clone 5B2, clone 201160 (Santa Cruz Biotechnology), clone M01, clone B1.1 (Abnova Corporation), clone EP449E (BioGenex), clone 6B8D1G5, clone 6B1C12F3 (Sino Biological), clone CL1297 (Atlas Antibodies), clone CC23 (Creative Diagnostics), clone TR66 (Enzo Life Sciences), clone MEM-92 (Cedarlane), clone EPR4516 (Origene Technologies), clone 3A12H2 (Proteintech Group), clone 33-2A3 (ALPCO), clone E272 (Biocare Medical), clone SP162, clone MRQ-39 (Sigma Aldrich), or clone F7.2.38 (Dako).

In some embodiments, the target protein may be a member of the CD28 family. In some embodiments, the target protein may be a member of the CD28 family such as PD-1 (CD279), LAG3 (CD223), ICOS (CD278), CTLA4 (CD152), BTLA (CD272) or CD28.

In some particular embodiments, the bispecific antibody or bispecific antigen binding fragment comprises an antigen binding domain capable of binding to CD3 or a CD3 polypeptide, and an antigen binding domain capable of binding to TIM-3 comprising at the CDRs, light and heavy chain variable domains or other TIM-3 binding fragment of clone 2C7 described herein.

In some embodiments, the bispecific antibody of the present invention may exhibit least one of the following properties:
  a) increases or enhances cell killing (e.g. T cell mediated cell killing) of TIM-3 expressing cells (antibody dependent cell-mediated cytotoxicity, ADCC), e.g. TIM-3 expressing acute myeloid leukemia cells;
  b) increases or enhances cell killing (e.g. T cell mediated cell killing) of TIM-3 expressing stem cells (antibody dependent cell-mediated cytotoxicity, ADCC), e.g. TIM-3 expressing, CD34+ acute myeloid leukemia cells;

In some embodiments, the antigen binding domain for PD-1 may comprise the CDRs, light and heavy chain variable domains or other PD-1 binding fragment of e.g. anti-PD-1 antibody clone J116, clone MIH4 (eBioscience), clone 7A11B1 (Rockland Immunochemicals Inc.), clone 192106 (R&D Systems), clone J110, clone J105 (MBL International), clone 12A7D7, clone 7A11B1 (Abbiotec), clone #9X21 (MyBioSource.com), clone 4H4D1 (Proteintech Group), clone D3W4U, clone D304S (Cell Signaling Technology), clone RMP1-30, clone RMP1-14 (Merck Millipore), clone EH12.2H7 (BioLegend), clone 10B1227 (United States Biological), clone UMAB198, or clone UMAB197 (Origene Technologies). In some embodiments, the antigen binding domain for LAG3 may comprise the CDRs, light and heavy chain variable domains or other LAG3 binding fragment of e.g. anti-LAG3 antibody clone 17B4 (Enzo Life Sciences), clone 333210 (R&D Systems), or clone 14L676 (United States Biological). In some embodiments, the antigen binding domain for ICOS may comprise the CDRs, light and heavy chain variable domains or other ICOS binding fragment of e.g. anti-ICOS antibody clone ISA-3 (eBioscience), clone SP98 (Novus Biologicals), clone 1G1, clone 3G4 (Abnova Corporation), clone 669222 (R&D Systems), clone TQ09 (Creative Diagnostics), or clone C398.4A (BioLegend). In some embodiments, the antigen binding domain for CTLA4 may comprise the CDRs, light and heavy chain variable domains or other CTLA4 binding fragment of e.g. anti-CTLA4 antibody clone 2F1, clone 1F4 (Abnova Corporation), clone 9H10 (EMD Millipore), clone BNU3 (GeneTex), clone 1E2, clone AS32 (LifeSpan BioSciences) clone A3.4H2.H12 (Acris Antibodies), clone 060 (Sino Biological), clone BU5G3 (Creative Diagnostics), clone MIH8 (MBL International), clone A3.6B10.G1, or clone L3D10 (BioLegend). In some embodiments, the antigen binding domain for BTLA may comprise the CDRs, light and heavy chain variable domains or other BTLA binding fragment of e.g. anti-BTLA antibody clone 1B7, clone 2G8, clone 4C5 (Abnova Corporation), clone 4B8 (antibodies-online), clone MIH26 (Thermo Scientific Pierce Antibodies), clone UMAB61 (OriGene Technologies), clone 330104 (R&D Systems), clone 1B4 (LifeSpan BioSciences), clone 440205, clone 5E7 (Creative Diagnostics). In some embodiments, the antigen binding domain for CD28 may comprise the CDRs, light and heavy chain variable domains or other CD28 binding fragment of e.g. anti-CD28 antibody clone CD28.6 (eBioscience), clone CD28.2, clone JJ319 (Novus Biologicals), clone 204.12, clone B-23, clone 10F3 (Thermo Scientific Pierce Antibodies), clone 37407 (R&D Systems), clone 204-12 (Abnova Corporation), clone 15E8 (EMD Millipore), clone 204-12, clone YTH913.12 (AbD Serotec), clone B-T3 (Acris Antibodies), clone 9H6E2 (Sino Biological), clone C28/77 (MyBioSource.com), clone KOLT-2 (ALPCO), clone 152-2E10 (Santa Cruz Biotechnology), or clone XPH-56 (Creative Diagnostics).

An antigen binding domain of a bispecific antibody or bispecific antigen binding fragment according to the present invention may be any domain of a polypeptide which is capable of binding to an antigen. In some embodiments, an antigen binding domain comprises at least the three light chain CDRs (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding domain may comprise the light chain variable domain and heavy chain variable domain of an antibody or antigen binding fragment. In some embodiments, an antigen binding domain may comprise the light chain polypeptide and heavy chain polypeptide of an antibody or antigen binding fragment.

Bispecific antibodies and bispecific antigen binding fragments according to the invention may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')$_2$-scFv$_2$), a bispecific Fc and $C_H3$ fusion protein (e.g. a taFv-Fc, Di-diabody, scDb-$C_H3$, scFv-Fc-scFv, HCAb-VHH, scFv-kih-Fc, or scFv-kih-$C_H3$), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

The skilled person is able to design and prepare bispecific antibodies and bispecific antigen binding fragments according to the present invention.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Homig and FArber-Schwarz), or French, How to make bispecific antibodies, Methods Mol. Med. 2000; 40:333-339, the entire contents of both of which are hereby incorporated by reference.

For example, a DNA construct encoding the light and heavy chain variable domains for the two antigen binding domains (i.e. the light and heavy chain variable domains for the antigen binding domain capable of binding TIM-3, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibodies, antigen fragments or polypeptides according to the present invention may also be used to construct chimeric antigen receptors (CAR; also called artificial T-cell receptors) in which a receptor is engineered by recombinant techniques to graft a selected specificity onto an immune cell. For example, the specificity of a monoclonal antibody may be grafted onto a T-cell, and the modified T-cells may find use in treatment of disease, e.g. cancer. One form of CAR is a fusion of an scFv comprising an antibody, antigen fragment or polypeptide according to the present invention to a transmembrane and endo domain of a suitable receptor scaffold. Techniques for the generation of CARs are described in Pule, M et al., (2003 Cytotherapy 5 (3): 211-26).

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Bio/Technology 10:779-783 (1992); Barbas et al. Proc Nat. Acad. Sci. USA 91:3809-

3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention preferably exhibit specific binding to TIM-3. An antibody that specifically binds to a target molecule preferably binds the target with greater affinity, and/or with greater duration than it binds to other targets. In one embodiment, the extent of binding of an antibody to an unrelated target is less than about 10% of the binding of the antibody to the target as measured, e.g., by ELISA, or by a radioimmunoassay (RIA). Alternatively, the binding specificity may be reflected in terms of binding affinity where the anti-TIM-3 antibody of the present invention binds to TIM-3 with a Kd that is at least 0.1 order of magnitude (i.e. $0.1 \times 10^n$, where n is an integer representing the order of magnitude) greater than the Kd of the antibody towards another target molecule, e.g. another member of the TIM-3 family. This may optionally be one of at least 0.2, 0.3, 0.4, 0.5, 0.6, 0.7, 0.8, 0.9, 1.0, 1.5, or 2.0.

Antibodies according to the present invention preferably have a dissociation constant (Kd) of one of $\leq 1\times10^{-6}$, $\leq 1\times10^{-5}$, $\leq 1\times10^{-5}$, or $\leq 1\times10^{-3}$. Binding affinity of an antibody for its target is often described in terms of its dissociation constant (Kd). Binding affinity can be measured by methods known in the art, such as by Surface Plasmon Resonance (SPR), or by a radiolabeled antigen binding assay (RIA) performed with the Fab version of the antibody and antigen molecule.

Antibodies according to the present invention may be "antagonist" antibodies that inhibit or reduce a biological activity of the antigen to which it binds. Blocking of TIM-3 assists in the restoration of T-cell function by inhibiting the immune-inhibitory signalling pathway mediated by TIM-3.

In some aspects, the antibody is 1B9, or a variant of 1B9. 1B9 comprises the following CDR sequences:

```
Light chain:
LC-CDR1:
                                        (SEQ ID NO: 10)
SGSSSNIGNNYVS

LC-CDR2:
                                        (SEQ ID NO: 11)
GNNWRPS

LC-CDR3:
                                        (SEQ ID NO: 12)
EAWDYYVAAGY

Heavy chain:
HC-CDR1:
                                        (SEQ ID NO: 30)
GGSFSGYYWS,
or
                                        (SEQ ID NO: 61)
GYYWS HC-CDR2:
                                        (SEQ ID NO: 31)
EINHSGSTNYNPSLKS

HC-CDR3:
                                        (SEQ ID NO: 32)
GYVAGSDA
```

CDR sequences determined by Kabat definition.

In some aspects, the antibody is 1H9, or a variant of 1H9. 1H9 comprises the following CDR sequences:

```
Light chain:
LC-CDR1:
                                        (SEQ ID NO: 10)
SGSSSNIGNNYVS

LC-CDR2:
                                        (SEQ ID NO: 11)
GNNWRPS

LC-CDR3:
                                        (SEQ ID NO: 13)
DSWDSADASGV

Heavy chain:
HC-CDR1:
                                        (SEQ ID NO: 30)
GGSFSGYYWS,
or
                                        (SEQ ID NO: 61)
GYYWS HC-CDR2:
                                        (SEQ ID NO: 31)
EINHSGSTNYNPSLKS

HC-CDR3:
                                        (SEQ ID NO: 33)
GYVAGFDD
```

CDR sequences determined by Kabat definition.

In some aspects, the antibody is 1H10, or a variant of 1H10. 1H10 comprises the following CDR sequences:

```
Light chain:
LC-CDR1:
                                        (SEQ ID NO: 10)
SGSSSNIGNNYVS

LC-CDR2:
                                        (SEQ ID NO: 11)
GNNWRPS

LC-CDR3:
                                        (SEQ ID NO: 14)
DSWDYDYAAGV

Heavy chain:
HC-CDR1:
                                        (SEQ ID NO: 30)
GGSFSGYYWS,
or
                                        (SEQ ID NO: 61)
GYYWS HC-CDR2:
                                        (SEQ ID NO: 31)
EINHSGSTNYNPSLKS

HC-CDR3:
                                        (SEQ ID NO: 34)
GYVAGFDS
```

CDR sequences determined by Kabat definition.

In some aspects, the antibody is 2C7, or a variant of 2C7. 2C7 comprises the following CDR sequences:

```
Light chain:
LC-CDR1:
                                        (SEQ ID NO: 10)
SGSSSNIGNNYVS

LC-CDR2:
                                        (SEQ ID NO: 11)
GNNWRPS
```

-continued
```
LC-CDR3:
                                         (SEQ ID NO: 15)
DSWDSYLAAGV Heavy chain:
HC-CDR1:
                                         (SEQ ID NO: 30)
GGSFSGYYWS,
or (SEQ ID NO: 61)
GYYWS HC-CDR2:
                                         (SEQ ID NO: 31)
EINHSGSTNYNPSLKS

HC-CDR3:
                                         (SEQ ID NO: 35)
GYVAGYDY
```

CDR sequences determined by Kabat definition.

In some aspects, the antibody is 2F4, or a variant of 2F4. 2F4 comprises the following CDR sequences:

```
Light chain:
LC-CDR1:
                                         (SEQ ID NO: 10)
SGSSSNIGNNYVS

LC-CDR2:
                                         (SEQ ID NO: 11)
GNNWRPS

LC-CDR3:
                                         (SEQ ID NO: 16)
ESWDYDYASGV

Heavy chain:
HC-CDR1:
                                         (SEQ ID NO: 30)
GGSFSGYYWS,
or (SEQ ID NO: 61)
GYYWS HC-CDR2:
                                         (SEQ ID NO: 31)
EINHSGSTNYNPSLKS

HC-CDR3:
                                         (SEQ ID NO: 36)
GYVAGSDA
```

CDR sequences determined by Kabat definition.

In some aspects, the antibody is 2G6, or a variant of 2G6. 2G6 comprises the following CDR sequences:

```
Light chain:
LC-CDR1:
                                         (SEQ ID NO: 10)
SGSSSNIGNNYVS

LC-CDR2:
                                         (SEQ ID NO: 11)
GNNWRPS

LC-CDR3:
                                         (SEQ ID NO: 17)
DSWDSSDSSGV

Heavy chain:
HC-CDR1:
                                         (SEQ ID NO: 30)
GGSFSGYYWS,
or (SEQ ID NO: 61)
GYYWS HC-CDR2:
                                         (SEQ ID NO: 31)
EINHSGSTNYNPSLKS

HC-CDR3:
                                         (SEQ ID NO: 37)
GYVAGFDS
```

CDR sequences determined by Kabat definition.

In some aspects, the antibody is 1D9, or a variant of 1D9. 1D9 comprises the following CDR sequences:

```
Light chain:
LC-CDR1:
                                         (SEQ ID NO: 10)
SGSSSNIGNNYV

LC-CDR2:
                                         (SEQ ID NO: 11)
GNNWRPS

LC-CDR3:
                                         (SEQ ID NO: 18)
EAWDSAYAAGS

Heavy chain:
HC-CDR1:
                                         (SEQ ID NO: 30)
GGSFSGYYWS,
or (SEQ ID NO: 61)
GYYWS HC-CDR2:
                                         (SEQ ID NO: 31)
EINHSGSTNYNPSLKS

HC-CDR3:
                                         (SEQ ID NO: 38)
GYYAGDDY
```

CDR sequences determined by Kabat definition.

In some aspects, the antibody is 1F4, or a variant of 1F4. 1F4 comprises the following CDR sequences:

```
Light chain:
LC-CDR1:
                                         (SEQ ID NO: 10)
SGSSSNIGNNYVS

LC-CDR2:
                                         (SEQ ID NO: 11)
GNNWRPS

LC-CDR3:
                                         (SEQ ID NO: 19)
DSWDAALSAGV

Heavy chain:
HC-CDR1:
                                         (SEQ ID NO: 30)
GGSFSGYYWS,
or (SEQ ID NO: 61)
GYYWS HC-CDR2:
                                         (SEQ ID NO: 31)
EINHSGSTNYNPSLKS
```

-continued

HC-CDR3:
GYVAGYDY (SEQ ID NO: 39)

CDR sequences determined by Kabat definition.

In some aspects, the antibody is 2C8, or a variant of 2C8. 2C8 comprises the following CDR sequences:

Light chain:
LC-CDR1:
SGSSSNIGNNYVS (SEQ ID NO: 10)

LC-CDR2:
GNNWRPS (SEQ ID NO: 11)

LC-CDR3:
ESWDAAAAAGY (SEQ ID NO: 20)

Heavy chain:
HC-CDR1:
GGSFSGYYWS, (SEQ ID NO: 30)
or
GYYWS (SEQ ID NO: 61)

HC-CDR2:
EINHSGSTNYNPSLKS (SEQ ID NO: 31)

HC-CDR3:
GYVAGSDA (SEQ ID NO: 40)

CDR sequences determined by Kabat definition.

Antibodies according to the present invention may comprise the CDRs of one of clones 1B9, 1H9, 1H10, 2C7, 2F4, 2G6, 1D9, 1F4, 2C8 or one of SEQ ID NOs 1 and 21, 2 and 22, 3 and 23, 4 and 24, 5 and 25, 6 and 26, 7 and 27, 8 and 28 or 9 and 29. In an antibody according to the present invention one or two or three or four of the six CDR sequences may vary. A variant may have one or two amino acid substitutions in one or two of the six CDR sequences.

Amino acid sequences of the $V_H$ and $V_L$ chains of ant-TIM-3 clones are shown in FIGS. 1 and 2. The encoding nucleotide sequences are shown in FIG. 4.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Le:franc (2001) "The Immunoglobulin Facts-Book", Academic Press, incorporated herein by reference.

In this specification, antibodies may have $V_H$ and/or VL chains comprising an amino acid sequence that has a high percentage sequence identity to one or more of the $V_H$ and/or $V_L$ amino acid sequences of SEQ ID NOs 1 and 21, 2 and 22, 3 and 23, 4 and 24, 5 and 25, 6 and 26, 7 and 27, 8 and 28 or 9 and 29 or to one or the amino acid sequences shown in FIGS. 1 and 2.

For example, antibodies according to the present invention include antibodies that bind TIM-3 and have a $V_H$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_H$ chain amino acid sequence of one of SEQ ID NOs 1 and 21, 2 and 22, 3 and 23, 4 and 24, 5 and 25, 6 and 26, 7 and 27, 8 and 28 or 9 and 29 or to one or the amino acid sequences shown in FIGS. 1 and 2.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Methods of Detection

Antibodies, or antigen binding fragments, described herein may be used in methods that involve the binding of the antibody or antigen binding fragment to TIM-3. Such methods may involve detection of the bound complex of antibody, or antigen binding fragment, and TIM-3. As such, in one embodiment a method is provided, the method comprising contacting a sample containing, or suspected to contain, TIM-3 with an antibody or antigen binding fragment as described herein and detecting the formation of a complex of antibody, or antigen binding fragment, and TIM-3.

Suitable method formats are well known in the art, including immunoassays such as sandwich assays, e.g. ELISA. The method may involve labelling the antibody, or antigen binding fragment, or TIM-3, or both, with a detectable label, e.g. fluorescent, luminescent or radio-label.

Methods of this kind may provide the basis of a method of diagnosis of a disease or condition requiring detection and or quantitation of TIM-3. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of TIM-3 present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of TIM-3 present in a patient sample may be indicative that a patient may respond to treatment with an anti-TIM-3 antibody. The presence of a high level of TIM-3 in a sample may be used to select a patient for treatment with an anti-TIM-3 antibody. The antibodies of the present invention may therefore be used to select a patient for treatment with anti-TIM-3 therapy.

Detection in a sample of TIM-3 may be used for the purpose of diagnosis of a T-cell dysfunctional disorder or a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

In one embodiment the level of TIM3 expression on CD8+ T cells may be detected in order to indicate the degree of T-cell exhaustion and severity of the disease state. In some cases, the level of TIM-3 expression on T cells or tumor cells may be used to select a patient for treatment with a modulator of TIM3 signalling, such as an anti-TIM3 antibody or anti-TIM3 agent.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

Therapeutic Applications

Antibodies, antigen binding fragments and polypeptides according to the present invention and compositions comprising such agents may be provided for use in methods of medical treatment. Treatment may be provided to subjects having a disease or condition in need of treatment. The disease or condition may be one of a T-cell dysfunctional disorder, including a T-cell dysfunctional disorder associated with a cancer, a cancer, or an infectious disease A T-cell dysfunctional disorder may be a disease or condition in which normal T-cell function is impaired causing downregulation of the subject's immune response to pathogenic antigens, e.g. generated by infection by exogenous agents such as microorganisms, bacteria and viruses, or generated by the host in some disease states such as in some forms of cancer (e.g. in the form of tumor associated antigens).

The T-cell dysfunctional disorder may comprise T-cell exhaustion or T-cell anergy. T-cell exhaustion comprises a state in which CD8$^+$ T-cells fail to proliferate or exert T-cell effector functions such as cytotoxicity and cytokine (e.g. IFNγ) secretion in response to antigen stimulation. Exhausted T-cells may also be characterised by sustained upregulation of TIM-3, where blockade of TIM-3:galectin 9 interactions may reverse the T-cell exhaustion and restore antigen-specific T cell responses.

The T-cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*. Examples of viral infections include infection with HIV, hepatitis B or hepatitis C.

The T-cell dysfunctional disorder may be associated with a cancer, such as tumor immune escape. Many human tumors express tumor-associated antigens recognised by T cells and capable of inducing an immune response. However, immune evasion is common and is believed to be mediated by a number of soluble factors, including galectin 9. As such, blocking the interaction of TIM-3 and galectin 9 may inhibit this negative immunoregulatory signal to tumor cells and enhance tumor-specific CD8$^+$ T-cell immunity.

Cancers may also be treated where there is no indication of a T-cell dysfunctional disorder such as T-cell exhaustion.

Antibodies according to the present invention may be cytotoxic against TIM-3 expressing cells, such as T-cells, e.g. exhausted T-cells or cancer cells such as acute myeloid leukemia cells. As such, the antibody, antigen binding fragment or polypeptides described herein may be useful in methods involving antibody dependent cell-mediated cytotoxicity (ADCC) or complement dependent cytotoxicity (CDC), or in any method that recruits immune effector functions to kill the target cells, sucha as CAR cells, or bispecific antibodies targeting CD3.

The use of an antibody, antigen binding fragment or polypeptide according to the present invention allows the subject to suppress TIM-3 signalling and mount an effective immune response with limited impairment, evasion or induction of tumor immune escape. In such treatments, the antibody, antigen binding fragment or polypeptide may provide a treatment for cancer that involves prevention of the development of tumor immune escape.

The treatment may be aimed at prevention of the T-cell dysfunctional disorder, e.g. prevention of infection or of the development or progression of a cancer. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of infection or development of cancer.

Treatment may comprise co-therapy with a vaccine, e.g. T-cell vaccine, which may involve simultaneous, separate or sequential therapy, or combined administration of vaccine and antibody, antigen binding fragment or polypeptide in a single composition. In this context, the antibody, antigen binding fragment or polypeptide may be provided as an adjuvant to the vaccine. Limited proliferative potential of exhausted T cells has been attributed as a main reason for failure of T-cell immunotherapy and combination an agent capable of blocking or reversing T cell exhaustion is a potential strategy for improving the efficacy of T-cell immunotherapy (Barber et al., *Nature* Vol 439, No. 9 p 682-687 February 2006).

Administration of an antibody, antigen binding fragment or polypeptide is preferably in a "therapeutically effective amount", this being sufficient to show benefit to the individual. The actual amount administered, and rate and timecourse of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies, antigen binding fragments and polypeptides according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment or polypeptide as described herein; and/or mixing an isolated antibody, antigen binding fragment or polypeptide as described herein with a pharmaceutically acceptable carrier, adjuvant, excipient or diluent.

For example, a further aspect of the present invention relates to a method of formulating or producing a medicament or pharmaceutical composition for use in the treatment of a T-cell dysfunctional disorder, the method comprising formulating a pharmaceutical composition or medicament by mixing an antibody, antigen binding fragment or polypeptide as described herein with a pharmaceutically acceptable carrier, adjuvant, excipient or diluent.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry *Nature Immunology* Vol. 12, No. 6, p 492-499, June 2011).

TIM-3 expression has been reported to play an important pathogenic role in patients having chronic infection (e.g. as reported by Golden-Mason L, et al., J Virol. 2009; 83(18): 9122-9130.)

Examples of bacterial infections that may be treated include infection by *Bacillus* spp., *Bordetella pertussis*, *Clostridium* spp., *Corynebacterium* spp., *Vibrio chloerae*, *Staphylococcus* spp., *Streptococcus* spp. *Escherichia, Klebsiella, Proteus, Yersinia, Erwina, Salmonella, Listeria* sp, *Helicobacter pylori*, mycobacteria (e.g. *Mycobacterium tuberculosis*) and *Pseudomonas aeruginosa* For example, the bacterial infection may be sepsis or tuberculosis.

Yao et al (PD-1 on dendritic cells impedes innate immunity against bacterial infection. *Blood* 113(23):5811-5818 Jun. 4, 2009) established PD-1 in the negative regulation of DC function during innate immune response to infection by *Listeria monocytogenes*. Brahmamdam et al (Delayed administration of anti-PD-1 antibody reverses immune dysfunction and improves survival during sepsis. *Journal of Leukocyte Biology* vo. 88, no. 2 233-240, August 2010) reported that anti-PD-1 antibody administered 24 h after sepsis prevented sepsis-induced depletion of lymphocytes and DCs, increased Bcl-xL, blocked apoptosis and improved survival. Tim3:Galectin-9 interactions have been reported to mediate T cell exhaustion and mediate the innate and adaptive immune response to infection by *Mycobacterium tuberculosis* (Jayaraman et al., *The Journal of Immunology* 2012, 188, 70.6).

Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

Chronic viral infections, such as those caused by HCV, HBV, and HIV commonly involve mechanisms to evade immune clearance. Expression of PD-1 and TIM-3 have been identified as correlating with defective T cell responses to hepatitis C virus (HCV) (McMahan et al., The Journal of Clinical Investigation Vol. 120, No. 12 p 4546-4557, December 2010). In HCV, McMahan et al (supra) found that the level of dual TIM-3 and PD-1 expression on HCV-specific CTLs predated the development of viral persistence, providing prognostic information. Barber et al. (Nature Vol 439, No. 9 p 682-687 February 2006) reported that PD-1 is upregulated during chronic viral infection. In mice infected with LCMV they reported that blockade of the PD-1/PD-L1 inhibitory pathway had a beneficial effect on CD8 T cells, restoring their ability to undergo proliferation, secrete cytokines, kill infected cells and decrease viral load. PD-1 is also upregulated in HIV infection (Said et al., *Nature Medicine Vol.* 16, No. 4 p 452-460 April 2010). Blocking interaction between PD-1 and PD-L1 contributed to viral clearance and improved T cell function in animal models of chronic viral infection (Said et al., supra).

Examples of fungal infections that may be treated include infection by *Altemaria* sp, *Aspergillus* sp, *Candida* sp and *Histoplasma* sp. The fungal infection may be fungal sepsis or histoplasmosis.

Chang et al (Blockade of the negative co-stimulatory molecules PD-1 and CTLA-4 improves survival in primary and secondary fungal sepsis. *Critical Care* 2013, 17:R85) reported that anti-PD1 antibodies were highly effective at improving survival in primary and secondary fungal sepsis. Lázár-Molnár et al (The PD-1/PD-L costimulatory pathway critically affects host resistance to the pathogenic fungus *Histoplasma capsulatum* PNAS vol. 105, no. 7, p 2658-2663, 19 Feb. 2008) reported that anti-PD-1 antibody significantly increased survival of mice infected with *Histoplasma capsulatum*. As such, the importance of T cell exhaustion in mediating fungal infection is well established. Examples of parasitic infections that may be treated include infection by *Plasmodium* species (e.g. *Plasmodium falciparum, Plasmodium yoeli, Plasmodium ovale, Plasmodium vivax*, or *Plasmodium chabaudi chabaudi*). The parasitic infection may be a disease such as malaria, leishmaniasis and toxoplasmosis.

Infection of humans with *Plasmodium falciparum* has been shown to result in higher expression of PD-1 and T cell exhaustion mice (Butler et al., *Nature Immunology* Vol. 13, No. 12, p 188-195 February 2012). Blockade of PD-L1 and LAG-3 using anti-PD-L1 and anti-LAG-3 monoclonal antibodies in vivo contributed to the restoration of CD4$^+$ T-cell function, amplification of the number of follicular helper T cells, germinal-center B cells and plasmablasts, enhanced protective antibodies and rapidly cleared blood-stage malaria in mice. It was also shown to block the development of chronic infection (Butler et al., supra).

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentume, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

Adoptive T Cell Transfer Therapy

Adoptive T cell transfer therapy generally refers to a process in which white blood cells are removed from a subject, typically by drawing a blood sample from which white blood cells are separated, expanded in vitro or ex vivo and returned either to the same subject or to a different subject. The treatment is typically aimed at increasing the amount/concentration of an active form of the required T cell population in the subject. Such treatment may be beneficial in subjects experiencing T cell exhaustion.

Antibodies capable of blocking the mechanism of T cell exhaustion, or reversing it, provide a means of enhancing T cell activity and promoting T cell expansion.

Accordingly, in a further aspect of the present invention a method is provided for expanding a population of T cells, wherein T cells are contacted in vitro or ex vivo with an antibody, antigen binding fragment or polypeptide according to the present invention.

The method may optionally comprise one or more of the following steps: taking a blood sample from a subject; isolating T cells from the blood sample; culturing the T cells in in vitro or ex vivo cell culture (where they may be contacted with the antibody, antigen binding fragment or polypeptide), collecting an expanded population of T cells; mixing the T cells with an adjuvant, diluent, or carrier; administering the expanded T cells to a subject.

Accordingly, in some aspects of the present invention a method of treatment of a subject having a T-cell dysfunctional disorder is provided, the method comprising obtaining a blood sample from a subject in need of treatment, culturing T cells obtained from the blood sample in the presence of an antibody, antigen binding fragment or polypeptide according to the present invention so as to expand the T cell population, collecting expanded T cells, and administering the expanded T cells to a subject in need of treatment.

The T cells may be obtained from a subject requiring treatment, and may be isolated and/or purified. They may be a CD4$^+$ and/or CD8$^+$ T-cell population. The T-cells may represent a population experiencing T cell exhaustion and may optionally have upregulated expression of TIM-3.

During culture, T cells may be contacted with the antibody, antigen binding fragment or polypeptide under conditions and for a period of time suitable to allow expansion of the T cells to a desired number of cells. After a suitable period of time the T cells may be harvested, optionally concentrated, and may be mixed with a suitable carrier, adjuvant or diluent and returned to the subject's body. A subject may undergo one or more rounds of such therapy.

Methods of T cell expansion are well known in the art, such as those described in Kalamasz et al., *J Immunother* 2004 September-October; 27(5):405-18; Montes et al., *Clin Exp Immunol* 2005 November; 142(2):292-302; Wölfl and Greenburg *Nature Protocols* 9 p 950-966 27 Mar. 2014; Trickett and Kwan *Journal of Immunological Methods* Vol. 275, Issues 1-2, 1 Apr. 2003, p 251-255; Butler et al *PLoSONE* 7(1) 12 Jan. 2012.

Simultaneous or Sequential Administration

Compositions may be administered alone or in combination with other treatments, either simultaneously or sequentially dependent upon the condition to be treated.

In this specification an antibody, antigen binding fragment or polypeptide of the present invention and an anti-infective agent or chemotherapeutic agent (therapeutic agent) may be administered simultaneously or sequentially.

In some embodiments, treatment with an antibody, antigen binding fragment or polypeptide of the present invention may be accompanied by chemotherapy.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

Anti-Infective Agents

In treating infection, an antibody, antigen binding fragment or polypeptide of the present invention may be administered in combination with an anti-infective agent, as described above. The anti-infective agent may be an agent known to have action against the microorganism or virus responsible for the infection.

Suitable anti-infective agents include antibiotics (such as penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins), anti-viral agents (such as reverse transcriptase inhibitors, integrase inhibitors, transcription factor inhibitors, antisense and siRNA agents and protease inhibitors), anti-fungal agents (such as polyenes, imidiazoles, triazoles, thiazoles, allylamines, and echinocandins) and anti-parasitic agents (such as antinematode agents, anticestode agents, antitrematode agents, antiamoebic agents and antiprotozoal agents).

Chemotherapy

Chemotherapy refers to treatment of a cancer with a drug or with ionising radiation (e.g. radiotherapy using X-rays or γ-rays). In preferred embodiments chemotherapy refers to treatment with a drug. The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a predetermined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from:
- alkylating agents such as cisplatin, carboplatin, mechlorethamine, cyclophosphamide, chlorambucil, ifosfamide;
- purine or pyrimidine anti-metabolites such as azathiopurine or mercaptopurine;
- alkaloids and terpenoids, such as *vinca* alkaloids (e.g. vincristine, vinblastine, vinorebine, vindesine), podophyllotoxin, etoposide, teniposide, taxanes such as paclitaxel (Taxolm), docetaxel;
- topoisomerase inhibitors such as the type I topoisomerase inhibitors camptothecins irinotecan and topotecan, or the type II topoisomerase inhibitorsamsacrine, etoposide, etoposide phosphate, teniposide;
- antitumor antibiotics (e.g. anthracyline antibiotics) such as dactinomycin, doxorubicin (Adriamycin™), epirubicin, bleomycin, rapamycin;
- antibody based agents, such as anti-PD-1 antibodies, anti-PD-L1, anti-CTLA-4, anti-LAG-3, anti-4-1BB, anti-GITR, anti-CD27, anti-BLTA, anti-OX40, anti-VEGF, anti-TNF-α, anti-IL-2, anti-GpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (MabtheraO), palivizumab, trastuzumab, etanercept, adalimumab, nimotuzumab
- EGFR inihibitors such as erlotinib, cetuximab and gefitinib
- anti-angiogenic agents such as bevacizumab (Avastin®)
- anti-cancer vaccines such as Sipuleucel-T (Provenge®)

In one embodiment the chemotherapeutic agent is an anti-PD-1 antibody or an anti-PD-L1, anti-CTLA-4, anti-LAG-3, anti-4-1BB, anti-GITR, anti-CD27, anti-BLTA, anti-OX40, anti-VEGF, anti-TNF-α, anti-IL-2, anti-GpIIb/IIIa, anti-CD-52, anti-CD20, anti-RSV, anti-HER2/neu (erB2) anti-TNF receptor, anti-EGFR antibody. In some embodiments, the chemotherapeutic agent is an immune checkpoint inhibitor or costimulation molecule.

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane®, Accutane®, Actinomycin-D Adriamycin®, Adrucil®, Afinitor®, Agrylin®, Ala-Cort®, Aidesleukin, Alemtuzumab, Alimta®, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU®, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU®, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen®, Dactinomycin, Darbepoetin Alfa, Dasatinib, Daunomycin, Daunorubicin, Daunorubicin Hydrochloride, Daunorubicin Liposomal, DaunoXome®, Decadron®, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux®, Erlotinib, *Erwinia* L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinb, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran™, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex™, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methyiprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navebine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraprod®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa™, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Veban®, Velcade®, VePesid®, Vesanoid®, Viadur™, Vidaza®, Vinblastine, Vinblastine Sulfate, Vincasar Pfs®, Vincristine, Vinorelbine, Vinorebine tartrate, VLB, VM-26™, Vorinostat, VP-16™, Vumon®, Xeloda®, Zanosar®, Zevalin™, Zinecard®, Zoladex®, Zoledronic acid, Zolinza®, Zometa®.

Routes of Administration

Antibodies, antigen binding fragments, polypeptides and other therapeutic agents, medicaments and pharmaceutical compositions according to aspects of the present invention may be formulated for administration by a number of routes, including but not limited to, parenteral, intravenous, intraarterial, intramuscular, subcutaneous, intradermal intratumoral and oral. Antibodies, antigen binding fragments, polypeptides and other therapeutic agents, may be formulated in fluid or solid form. Fluid formulations may be formulated for administration by injection to a selected region of the human or animal body.

Dosage Regime

Multiple doses of the antibody, antigen binding fragment or polypeptide may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment or polypeptide. The kit may provide the antibody, antigen binding fragment or polypeptide in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Protein Expression

Molecular biology techniques suitable for the producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 1. Light chain variable domain sequences for anti-TIM-3 antibody 1B9, 1H9, 1H10, 2C7, 2F4, 2G6, 1D9, 1F4, 2C8 (human IgG4). CDRs are underlined and shown separately.

FIG. 2. Heavy chain variable domain sequences for anti-TIM-3 antibody clones 1B9, 1H9, 1H10, 2C7, 2F4, 2G6, 1D9, 1F4, 2C8 (human IgG4). CDRs are underlined and shown separately.

FIG. 3. Table showing light chain and heavy chain CDR sequences for anti-TIM-3 antibody clones 1B9, 1H9, 1H10, 2C7, 2F4, 2G6, 1D9, 1F4, 2C8.

FIG. 4. Nucleotide and encoded amino acid sequences of heavy and light chain variable domain sequences for anti-TIM-3 antibody clones 1B9, 1H9, 1H10, 2C7, 2F4, 2G6, 1 D9, 1F4, 2C8 (human IgG4).

FIG. 5. Table showing off rates of clones 1B9, 1H9, 1H10, 2C7, 2F4, 2G6, 1 D9, 1F4, 2C8.

EXAMPLES

Isolation of Anti-Human TIM-3 Antibodies

Anti-TIM-3 antibodies were isolated from a human antibody phage display library via in vitro selection in a 3-round bio-panning process.

Basically, streptavidin-magnetic beads were coated with biotinylated human TIM-3 and used to fish-out anti-TIM-3-specific phages using magnetic sorting. Some steps to get rid of potential anti-biotin antibodies were added in the selection process.

After a small-scale induction in HB2151 cells, Fab antibodies were screened by ELISA. Briefly, ELISA plates were coated with human Tim-3 and blocked with a solution of casein. After extensive washes in PBS Tween-20, supernatants from induction plates were transferred into the ELISA plates in the presence of 7% milk in PBS. After 90 minutes at room temperature under agitation and extensive washes, a goat anti-human Fab antibody coupled to HRP was added. One hour later, plates were washed and TMB substrate added. The reaction was stopped with 1M HCl and optical density measured at 450 nm with a reference at 670 nm. Antibodies giving an absorbance >0.1 were selected as positive. A first clonality screening was performed by DNA fingerprinting; clonality was then confirmed by sequencing.

Affinity Maturation

One clone showing a good profile in neutralising TIM-3 in vitro was further engineered. After reverting its sequence to a germline-like framework, this antibody went through affinity maturation by CDR engineering. Selection of specific affinity-matured anti-TIM-3 antibodies was conducted by phage display, and screening by ELISA.

In order to select some leads amongst the ELISA-positive clones, TIM-3 association/dissociation profiles were analysed by Surface Plasmon Resonance (SPR). Briefly, human TIM-3 coupled to Fc was immobilised on sensor chip and the antibodies were then applied as a flow onto the chip. Association and dissociation rates were recorded using a ProteOn XPR36 bioanalyser (Biorad). Nine clones (1B9, 1H9, 1H10, 2C7, 2F4, 2G6, 1 D9, 1F4, 2C8) were selected based on their rapid/strong association to TIM-3 and their slow dissociation from the protein (FIG. 5).

Specific Killing by Bispecific Anti-TIM-3, Anti-CD3 Antibody of Acute Myeloid Leukemia Cells from Patients Anti-TIM-3 clone 2C7 was used to construct a bi-specific antibody able to engage T cells on one side (specificity for CD3) and target TIM-3 on the other side. The bispecific antibody comprises two single chain variable Fragments (scFvs) as a fusion protein. One of the scFvs comprises the $V_H$ and $V_L$ sequences for clone 2C7 (i.e. SEQ ID NOs: 4 and 24), and the other scFv comprises the $V_H$ and $V_L$ sequences for an anti-CD3 antibody clone.

Figure 8:
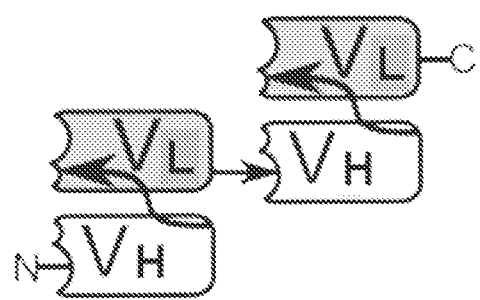
FIG. 8. Schematic drawing of the tandem single chain bispecific antibody format.

The format for the tandem single chain bispecific antibody is shown in FIG. 8.

Anti-TIM-3 clone 2C7, in tandem single-chain bispecific format with anti-CD3 (anti-TIM-3 clone 2C7-anti CD3 bispecific antibody), was then tested to assess its ability to kill Acute Myeloid Leukamia (AML) cells obtained from AML patients' biopsies.

Briefly, purified T cells were mixed with AML cells obtained from patients refractory to 3 lines of chemotherapy treatment, at a ratio of 1:1. The bispecific antibody was added at various concentrations, and the mixture was incubated for 24 hours. After incubation, lysis of AML cells was measured.

Figure 6:
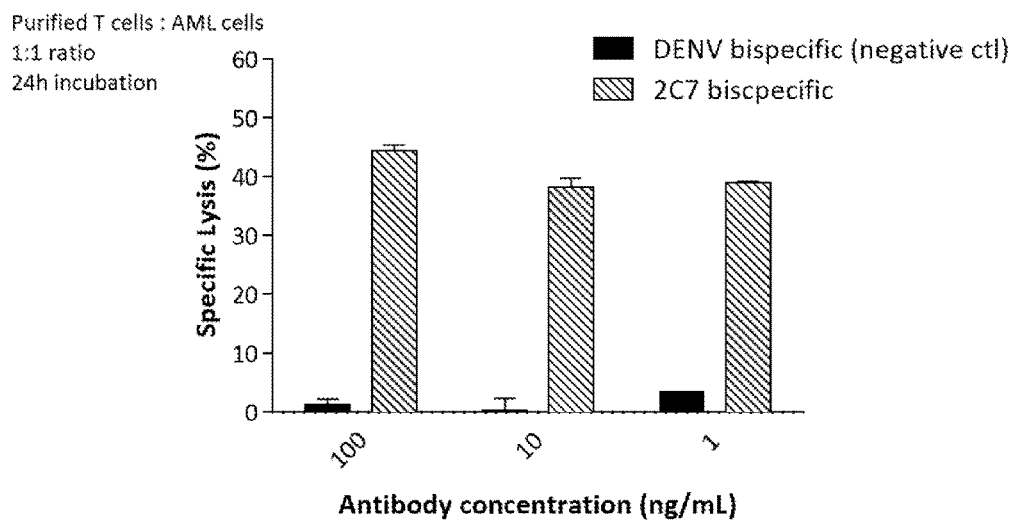
FIG. 6. Chart showing effect of anti-TIM-3 clone 2C7-anti CD3 bispecific antibody on purified T cells and acute myeloid leukemia (AML) cells. AML cells were mixed with purified T cells at a 1:1 ratio and the antibody was added at various concentrations. After 24-hour incubation, lysis was measured.

The results are shown in FIG. 6. Anti-TIM-3 clone 2C7-anti CD3 bispecific antibody proved to be potent in killing AML cells from chemotherapy-refractory patients ex vivo.

The clone 2C7-anti CD3 bispecific antibody was then tested on AML stem cells, i.e. cells within the AML biopsies that express high levels of CD34. After selection, CD34+ cells (samples >99% CD34+ purity) were mixed with purified T cells at a 1:1 ratio and the antibody was added at various concentrations. After 24-hour incubation, lysis was measured.

Figure 7:
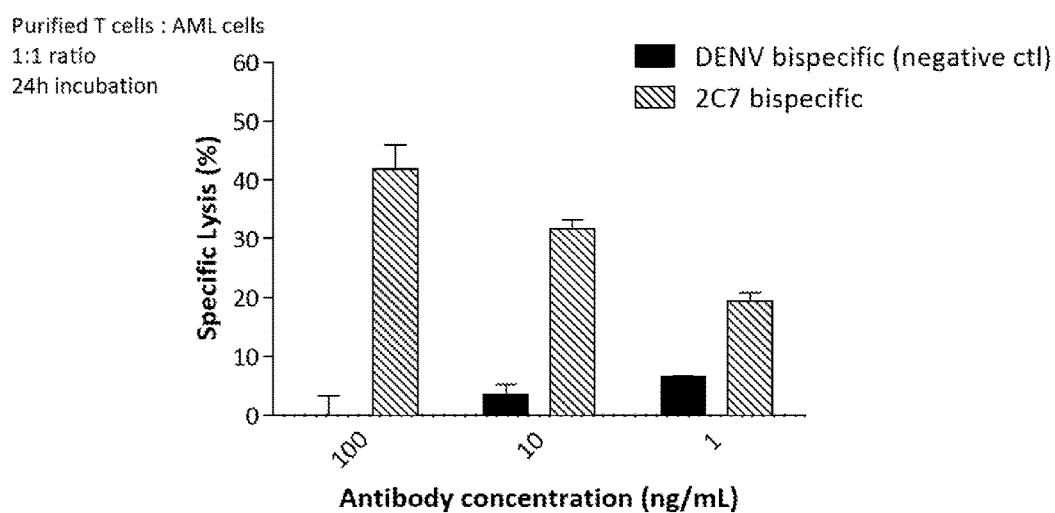
FIG. 7. Chart showing CD34 specific killing effect of anti-TIM-3 clone 2C7-anti CD3 bispecific antibody on CD34+ cells in AML biopsies (i.e. AML stem cells). After selection, CD34+ cells (samples >99% CD34+ purity) were mixed with purified T cells at a 1:1 ratio and the antibody was added at various concentrations. After 24-hour incubation, lysis was measured.

The results are shown in FIG. 7. Anti-TIM-3 clone 2C7-anti CD3 bispecific antibody showed an ability to kill AML stem cells ex vivo, at medium to high concentrations.

The invention claimed is:

1. An antibody that binds to TIM-3 or an antigen binding fragment of the antibody having:

(i) at least one light chain variable region incorporating the following CDRs:

LC-CDR1:
SGSSSNIGNNYVS          (SEQ ID NO: 10)

LC-CDR2:
GNNWRPS                (SEQ ID NO: 11)

LC-CDR3:
EAWDYYVAAGY;           (SEQ ID NO: 12)

and at least one heavy chain variable region incorporating the following CDRs:

HC-CDR1:
GYYWS,                 (SEQ ID NO: 61)
or
GGSFSGYYWS             (SEQ ID NO: 30)

HC-CDR2:
EINHSGSTNYNPSLKS       (SEQ ID NO: 31)

HC-CDR3:
GYVAGSDA;              (SEQ ID NO: 30)

OR (ii) at least one light chain variable region incorporating the following CDRs:

LC-CDR1:
SGSSSNIGNNYVS          (SEQ ID NO: 10)

LC-CDR2:
GNNWRPS                (SEQ ID NO: 11)

LC-CDR3:
DSWDSADASGV;           (SEQ ID NO: 13)

and at least one heavy chain variable region incorporating the following CDRs:

HC-CDR1:
GYYWS,                 (SEQ ID NO: 61)
or
GGSFSGYYWS             (SEQ ID NO: 30)

HC-CDR2:
EINHSGSTNYNPSLKS       (SEQ ID NO: 31)

HC-CDR3:
GYVAGFDD;              (SEQ ID NO: 33)

OR (iii) at least one light chain variable region incorporating the following CDRs:

LC-CDR1:
SGSSSNIGNNYVS          (SEQ ID NO: 10)

LC-CDR2:
GNNWRPS                (SEQ ID NO: 11)

-continued

```
LC-CDR3:
                                    (SEQ ID NO: 14)
DSWDYDYAAGV;
``` and
at least one heavy chain variable region incorporating the following CDRs:

```
HC-CDR1:
                                    (SEQ ID NO: 61)
GYYWS,
or
                                    (SEQ ID NO: 30)
GGSFSGYYWS

HC-CDR2:
                                    (SEQ ID NO: 31)
EINHSGSTNYNPSLKS

HC-CDR3:
                                    (SEQ ID NO: 34)
GYVAGFDS;
```

OR (iv) at least one light chain variable region incorporating the following CDRs:

```
LC-CDR1:
                                    (SEQ ID NO: 10)
SGSSSNIGNNYVS

LC-CDR2:
                                    (SEQ ID NO: 11)
GNNWRPS

LC-CDR3:
                                    (SEQ ID NO: 15)
DSWDSYLAAGV;
``` and
at least one heavy chain variable region incorporating the following CDRs:

```
HC-CDR1:
                                    (SEQ ID NO: 61)
GYYWS,
or
                                    (SEQ ID NO: 30)
GGSFSGYYWS

HC-CDR2:
                                    (SEQ ID NO: 31)
EINHSGSTNYNPSLKS

HC-CDR3:
                                    (SEQ ID NO: 35)
GYVAGYDY;
```

OR (v) at least one light chain variable region incorporating the following CDRs:

```
LC-CDR1:
                                    (SEQ ID NO: 10)
SGSSSNIGNNYVS

LC-CDR2:
                                    (SEQ ID NO: 11)
GNNWRPS
```

-continued

```
LC-CDR3:
                                    (SEQ ID NO: 16)
ESWDYDYASGV;
``` and
at least one heavy chain variable region incorporating the following CDRs:

```
HC-CDR1:
                                    (SEQ ID NO: 61)
GYYWS,
or
                                    (SEQ ID NO: 30)
GGSFSGYYWS

HC-CDR2:
                                    (SEQ ID NO: 31)
EINHSGSTNYNPSLKS

HC-CDR3:
                                    (SEQ ID NO: 36)
GYVAGSDA;
```

OR (vi) at least one light chain variable region incorporating the following CDRs:

```
LC-CDR1:
                                    (SEQ ID NO: 10)
SGSSSNIGNNYVS

LC-CDR2:
                                    (SEQ ID NO: 11)
GNNWRPS

LC-CDR3:
                                    (SEQ ID NO: 17)
DSWDSSDSSGV;
``` and
at least one heavy chain variable region incorporating the following CDRs:

```
HC-CDR1:
                                    (SEQ ID NO: 61)
GYYWS,
or
                                    (SEQ ID NO: 30)
GGSFSGYYWS

HC-CDR2:
                                    (SEQ ID NO: 31)
EINHSGSTNYNPSLKS

HC-CDR3:
                                    (SEQ ID NO: 37)
GYVAGFDS;
```

OR (vii) at least one light chain variable region incorporating the following CDRs:

```
LC-CDR1:
                                    (SEQ ID NO: 10)
SGSSSNIGNNYVS

LC-CDR2:
                                    (SEQ ID NO: 11)
GNNWRPS
```

-continued

```
LC-CDR3:
                              (SEQ ID NO: 18)
EAWDSAYAAGS;
``` and
at least one heavy chain variable region incorporating the following CDRs:

```
HC-CDR1:
                              (SEQ ID NO: 61)
GYYWS,
or
                              (SEQ ID NO: 30)
GGSFSGYYWS

HC-CDR2:
                              (SEQ ID NO: 31)
EINHSGSTNYNPSLKS

HC-CDR3:
                              (SEQ ID NO: 38)
GYYAGDDY;
```

OR (viii) at least one light chain variable region incorporating the following CDRs:

```
LC-CDR1:
                              (SEQ ID NO: 10)
SGSSSNIGNNYVS

LC-CDR2:
                              (SEQ ID NO: 11)
GNNWRPS

LC-CDR3:
                              (SEQ ID NO: 19)
DSWDAALSAGV;
``` and
at least one heavy chain variable region incorporating the following CDRs:

```
HC-CDR1:
                              (SEQ ID NO: 61)
GYYWS,
or
                              (SEQ ID NO: 30)
GGSFSGYYWS

HC-CDR2:
                              (SEQ ID NO: 31)
EINHSGSTNYNPSLKS

HC-CDR3:
                              (SEQ ID NO: 39)
GYVAGYDY;
```

OR (ix) at least one light chain variable region incorporating the following CDRs:

```
LC-CDR1:
                              (SEQ ID NO: 10)
SGSSSNIGNNYVS

LC-CDR2:
                              (SEQ ID NO: 11)
GNNWRPS
```

-continued

```
LC-CDR3:
                              (SEQ ID NO: 20)
ESWADAAAAGY;
``` and
at least one heavy chain variable region incorporating the following CDRs:

```
HC-CDR1:
                              (SEQ ID NO: 61)
GYYWS,
or
                              (SEQ ID NO: 30)
GGSFSGYYWS

HC-CDR2:
                              (SEQ ID NO: 31)
EINHSGSTNYNPSLKS

HC-CDR3:
                              (SEQ ID NO: 40)
GYVAGSDA.
```

2. The TIM-3 binding antibody or the antigen binding fragment of the antibody of claim 1, comprising a heavy chain and a light chain variable region sequence, wherein:
the heavy chain sequence has at least 85% sequence identity to the heavy chain sequence of one of SEQ ID NOs: 21 to 29 (FIG. 2), and
the light chain sequence has at least 85% sequence identity to the light chain sequence of one of: SEQ ID NO:1 to 9 (FIG. 1).

3. The TIM-3 binding antibody or the antigen binding fragment of the antibody of claim 1, which is a bispecific antibody or a bispecific antigen binding fragment of the antibody, further comprising an antigen binding domain which binds to a target protein other than TIM-3.

4. The TIM-3 binding antibody or the antigen binding fragment of the antibody of claim 3, wherein the antigen binding domain which binds to a target protein other than TIM-3 binds to CD3 or a CD3 polypeptide.

5. The TIM-3 binding antibody or the antigen binding fragment of the antibody of claim 4, wherein the antibody or the antigen binding fragment of the antibody is cytotoxic against TIM-3 expressing cells.

6. The TIM-3 binding antibody or the antigen binding fragment of the antibody of claim 1, comprising a heavy chain and a light chain variable region sequence, wherein:
(i) the heavy chain sequence has at least 85% sequence identity to the heavy chain sequence of SEQ ID NO:21, and
the light chain sequence has at least 85% sequence identity to the light chain sequence of SEQ ID NO:1;
OR
(ii) the heavy chain sequence has at least 85% sequence identity to the heavy chain sequence of SEQ ID NO:22, and
the light chain sequence has at least 85% sequence identity to the light chain sequence of SEQ ID NO:2;
OR
(iii) the heavy chain sequence has at least 85% sequence identity to the heavy chain sequence of SEQ ID NO:23, and the light chain sequence has at least 85% sequence identity to the light chain sequence of SEQ ID NO:3;

OR (iv) the heavy chain sequence has at least 85% sequence identity to the heavy chain sequence of SEQ ID NO:24, and the light chain sequence has at least 85% sequence identity to the light chain sequence of SEQ ID NO:4;

OR (v) the heavy chain sequence has at least 85% sequence identity to the heavy chain sequence of SEQ ID NO:25, and the light chain sequence has at least 85% sequence identity to the light chain sequence of SEQ ID NO:5;

OR (vi) the heavy chain sequence has at least 85% sequence identity to the heavy chain sequence of SEQ ID NO:26, and the light chain sequence has at least 85% sequence identity to the light chain sequence of SEQ ID NO:6;

OR (vii) the heavy chain sequence has at least 85% sequence identity to the heavy chain sequence of SEQ ID NO:27, and the light chain sequence has at least 85% sequence identity to the light chain sequence of SEQ ID NO:7;

OR (viii) the heavy chain sequence has at least 85% sequence identity to the heavy chain sequence of SEQ ID NO:28, and the light chain sequence has at least 85% sequence identity to the light chain sequence of SEQ ID NO:8;

OR (ix) the heavy chain sequence has at least 85% sequence identity to the heavy chain sequence of SEQ ID NO:29, and the light chain sequence has at least 85% sequence identity to the light chain sequence of SEQ ID NO:9.

7. The TIM-3 binding antibody or the antigen binding fragment of the antibody of claim 1, wherein the antigen binding fragment is a Fab fragment or scFv fragment.

8. The TIM-3 binding antibody or the antigen binding fragment of the antibody of claim 1, wherein the antibody comprises a human constant region selected from IgG1, IgG2, IgG3 and IgG4.

9. A chimeric antigen receptor (CAR) comprising the TIM-3 binding antibody or the antigen binding fragment of the antibody of claim 1.

* * * * *